(12) United States Patent
Skands et al.

(10) Patent No.: US 10,048,190 B2
(45) Date of Patent: Aug. 14, 2018

(54) MICROFLUIDIC PARTICLE ANALYSIS DEVICE

(71) Applicant: SBT Instruments ApS, Herlev (DK)

(72) Inventors: Gustav Erik Skands, Frederiksberg (DK); Christian Vinther Bertelsen, Frederiksberg (DK)

(73) Assignee: SBT INSTRUMENTS APS, Herlev (DK)

( * ) Notice: Subject to any disclaimer, the term of this patent is extended or adjusted under 35 U.S.C. 154(b) by 0 days.

(21) Appl. No.: 15/543,498

(22) PCT Filed: Jan. 21, 2016

(86) PCT No.: PCT/EP2016/051185
§ 371 (c)(1),
(2) Date: Jul. 13, 2017

(87) PCT Pub. No.: WO2016/116535
PCT Pub. Date: Jul. 28, 2016

(65) Prior Publication Data
US 2017/0370819 A1    Dec. 28, 2017

(30) Foreign Application Priority Data
Jan. 21, 2015   (EP) ..................................... 15151970

(51) Int. Cl.
*G01R 27/08*    (2006.01)
*G01N 15/10*    (2006.01)
(Continued)

(52) U.S. Cl.
CPC ....... *G01N 15/1031* (2013.01); *G01N 1/2035* (2013.01); *G01N 15/0656* (2013.01); *G01N 15/1056* (2013.01); *G01N 2001/2064* (2013.01)

(58) Field of Classification Search
None
See application file for complete search history.

(56) References Cited

U.S. PATENT DOCUMENTS 6,169,394 B1 * 1/2001 Frazier ............... G01N 27/4473
324/692
6,437,551 B1   8/2002 Krulevitch et al.
(Continued)

FOREIGN PATENT DOCUMENTS

CA    2523094 A1 * 11/2004  .......... H01J 49/0018
EP    1 335 198 A1    8/2003
(Continued)

OTHER PUBLICATIONS

International Search Report issued in connection with PCT International Application No. PCT/EP2016/051185.
(Continued)

*Primary Examiner* — Daniel Miller
(74) *Attorney, Agent, or Firm* — John P. White; Cooper & Dunham LLP

(57) ABSTRACT

A microfluidic particle analysis device comprising an inlet with an inlet manifold providing parallel fluid communication with a bypass channel and a measuring channel having a sensor system for detecting a particle, wherein the angle of the measuring channel relative to the main flow direction is in the range of 0° to 60°, and wherein the angle of the bypass channel relative to the main flow direction is in the range of 0° to 60°. The present invention also relates to a method of using the device microfluidic particle analysis.

22 Claims, 7 Drawing Sheets

(51) Int. Cl.
    *G01N 1/20*    (2006.01)
    *G01N 15/06*   (2006.01)

(56) References Cited

U.S. PATENT DOCUMENTS

| | | | |
|---|---|---|---|
| 9,366,606 B1 * | 6/2016 | McPeak | G01N 1/38 |
| 2002/0081744 A1 | 6/2002 | Chan et al. | |
| 2006/0018790 A1 | 1/2006 | Naka et al. | |
| 2010/0022680 A1 * | 1/2010 | Karnik | A61K 9/5153 523/105 |
| 2010/0116647 A1 | 5/2010 | Kornmuller | |
| 2013/0074586 A1 | 3/2013 | Blanco-gomez et al. | |
| 2013/0295602 A1 * | 11/2013 | Fowler | C12Q 1/686 435/34 |

FOREIGN PATENT DOCUMENTS

| | | |
|---|---|---|
| EP | 1 528 387 A2 | 5/2005 |
| WO | WO 00/17630 A1 | 3/2000 |
| WO | WO 01/14865 A1 | 3/2001 |
| WO | WO 03/048728 A2 | 6/2003 |
| WO | WO 2005/118138 A1 | 12/2005 |
| WO | WO 2007/088517 A2 | 8/2007 |
| WO | WO 2012/056334 A1 | 5/2012 |
| WO | WO 2013/181453 A2 | 12/2013 |
| WO | WO 2013/190326 A2 | 12/2013 |

OTHER PUBLICATIONS

Written Opinion of the International Searching Authority issued in connection with PCT International Application No. PCT/EP2016/051185.

Extended European Search Report issued in connection with European Patent Application No. EP 15151970.9-1553.

Shady Gawad, et al., "Dielectric spectroscopy in a micromachined flow cytometer: theoretical and practical considerations", Lab on a Chip, Feb. 25, 2004, Issue 3, pp. 241-251.

Karen Cheung, et al., "Impedance Spectroscopy Flow Cytometry: On-Chip Label-Free Cell Differentiation", Cytometry Part A, Jun. 2005, 65(2), pp. 124-132.

Timothée Houssin, et al., "Electrochemical impedance spectroscopy for detection of parasites in drinking water", IEEE Sensors, 2009, Conference, Christchurch, New Zealand.

Karen Cheung, et al., "Microfluidic Impedance-Based Flow Cytometry", Cytometry Part A, Jul. 2010, 77(7), pp. 648-666.

F. David, et al., "Viability and Membrane Potential Analysis of *Bacillus magaterium* Cells by Impedance Flow Cytometry", Biotechnology and Bioengineering, Feb. 2012, vol. 109, No. 2, pp. 483-492.

Elisabeth Ariel Ring, "Design and Characterization of a Microfluidic System for Scanning Transmission Electron Microscopy", Thesis submitted to the Faculty of the Graduate School of Vanderbilt University, Aug. 2010, Nashville, TN, US.

* cited by examiner

MICROFLUIDIC PARTICLE ANALYSIS DEVICE

CROSS-REFERENCE TO RELATED APPLICATIONS

This application is a § 371 national stage of PCT International Application No. PCT/EP2016/051185, filed Jan. 21, 2016, claiming priority of European Patent Application No. EP 15151970.9, filed Jan. 21, 2015, the contents of each of which are hereby incorporated by reference into the application.

FIELD OF THE INVENTION

The present invention relates to a microfluidic particle analysis device and to a method of detecting a particle in a fluid using the microfluidic particle analysis device. The device is useful for detecting and quantifying bacteria in drinking water, industrial process streams and in other liquids of similar viscosity.

PRIOR ART

Analysis of drinking water is a field where no sufficiently fast technologies currently exist that allow detection of harmful bacteria in drinking water in order to prevent pollution of water supplies to households. Current bacteria tests typically require incubation which means that the fastest tests take at least 24 hours to provide results. Analysis methods that can give an indication of the bacteria level in a couple of hours do exist, but they do not provide exact quantitative results. In all cases, manual extraction is required and extracted samples must be sent to a laboratory. This severely limits the testing frequency due to high costs associated with having people taking samples.

In water utilities this means that water infected with dangerous bacteria will be supplied to citizens long before the test results are available. Bacterial contaminations can lead to infections involving vomiting and influenza-like symptoms, which often require hospitalisation. As a consequence of the slow analyses, pollutions of drinking water are often not discovered before citizens get sick.

Furthermore, in the case of the food and pharmaceutical industries large amounts of money are wasted for companies having to call back batches of product if it is not discovered in time that infected water has been used in the production of the product.

There is therefore a great need for real-time monitoring of drinking water for bacterial contamination.

Several technologies exist for detecting particles, such as bacteria, suspended in a liquid. A commonly employed technology for detecting and quantifying cells in liquid in a laboratory is electrical impedance spectroscopy (EIS). Thus, for example the review article Cheung et al. 2010 (*Cytometry Part A*, 2010, 77A: 648-666) summarises the background knowledge within the use of EIS in microfluidic systems.

Gawad et al. (*Lab Chip*, 2004, 4: 241-251) present theoretical considerations for a microfluidic flow cytometer using EIS to analyse cells. Characterisation of cells of approximately suspended in KCl solutions of 12,880 $\mu$S/cm conductivity is suggested, but no practical examples are shown.

The work of Gawad et al. is implemented into practice by Cheung et al. 2005 (*Cytometry Part A*, 2005, 65A:124-132). Cheung at al. 2005 study differentiation of red blood cells and derived components and beads of comparable sizes (i.e. about 5 $\mu$m in diameter). The fabrication and test of a microfluidic device are demonstrated, and it is shown how EIS using two different frequencies can be performed using the device. The device uses a flow-rate of 10 mm/s, and cells are suspended in phosphate buffered saline of high conductivity.

Houssin et al. (*IEEE SENSORS* 2009 *Conference*, 396-399) report the use of EIS in a microdevice for analysing oocysts of a parasite of the species *Cryptosporidium parvum* in water of low conductivity. David et al. (*Biotechnology and Bioengineering*, 2011, 109: 483-492) provide a comparison between flow cytometry and microfluidic EIS.

While several examples of microfluidic EIS devices exist neither appear suited for the analysis of drinking water. In particular, the facts that drinking water has low conductivity and that the bacteria are present in very low amounts compared to characterising samples where cells may have been added to a known concentration make it problematic to implement EIS for analysing drinking water. Moreover, the analysis of drinking water requires processing of excessive volumes of sample liquid and since EIS requires electrodes at a distance only a few times the size of the particle of interest there is a scale mismatch between EIS and the analysis of drinking water.

US 2002/081744 discloses methods and apparatuses for the characterisation of single polymers, e.g. for determination of the velocities of single elongated polymers, the length and molecular mass of single polymers, or the distance between landmarks on single polymers. The methods are based on time-correlated measurements of an elongated macromolecule at each of a plurality of detection zones, which are located along the travel path of the elongated macromolecule at predetermined spacings. Signal amplitude profiles, e.g, intensity-time curves when fluorescence based measurements are used, of an elongated macromolecule are measured as the macromolecule passes through each of the detection zones. The apparatus contains a channel having a delivery region and a region of polymer elongation, where the delivery region is a "wide channel" having a diameter in the range of 1 to 1000 $\mu$m, and the region of polymer elongation is preferred to have a funnel reducing the height of a channel from 1 $\mu$m to 0.25 $\mu$m. When operated with a syringe pump the system may comprise a bypass channel reducing the flow rate to under 1 pL/s. The system of US 2002/081744 is neither suited for analysis of microparticles nor for use as a flow system.

US 2010/116647 discloses a macroscale water treatment plant, e.g. a ballast water treatment plant, for removing sediments and/or removing and/or destroying living organisms, which has at least one filter unit and at least one disinfecting unit. The system may have a bypass.

E. A. Ring, Design And Characterization Of A Microfluidic System For Scanning Transmission Electron Microscopy (Thesis Submitted to the Faculty of the Graduate School of Vanderbilt University, August, 2010) discloses a system intended for understanding cellular processes on a molecular level, which is scaled to allow electron microscopy on a sample and further to allow exchange of fluid on the scale of seconds or minutes. The system has a main channel and a bypass channel, which is larger than the main channel, where the main channel has a window for observing cells. However, the methods employed to construct the system have insufficient tolerances for creating a system useful for the analysis of particles in a flowing stream, and in particular the available tolerances do not allow the manufacture of a system for quantification of cells.

In light of the above it is an aim of the present invention to provide a microfluidic device for monitoring drinking water and other liquids with similar viscosities, which allows the detection of bacteria, in particular using EIS technology. The continuous monitoring of drinking water over extended periods of time is especially relevant and the present invention seeks to address this issue.

DISCLOSURE OF THE INVENTION

The present invention relates to a microfluidic particle analysis device comprising an inlet in fluid communication via a main channel defining a main flow direction with an inlet manifold providing parallel fluid communication with
a bypass channel of hydrodynamic resistance $R_{bypass}$, and
a measuring channel of hydrodynamic resistance $R_{measuring}$, the measuring channel having a cross-sectional dimension in the range of from 1 µm to 50 µm and further having a sensor system for detecting a particle,
wherein a flow distribution parameter $X_{measuring} = R_{measuring}^{-1}(R_{measuring}^{-1} + R_{bypass}^{-1})^{-1}$ is in the range of from $10^{-6}$ to 0.25, wherein the angle of the measuring channel relative to the main flow direction is in the range of 0° to 60°, and wherein the angle of the bypass channel relative to the main flow direction is in the range of 0° to 60°, and
the microfluidic particle analysis device further comprising an outlet in fluid communication with the bypass channel and the measuring channel.

In use a flow of liquid is led through the microfluidic particle analysis device, i.e. from the inlet to the outlet, and the liquid flowing through the microfluidic particle analysis device is analysed for a content of particles, e.g. the particles are "detected". The microfluidic particle analysis device can also be referred to as a flow system.

In general, a sensor for detecting particles requires the particle to pass the sensor at a limited flow rate for the particle to be detected, and with the present invention the microfluidic particle analysis device may be designed to match a desired sensor, since the flow distribution parameter $X_{measuring}$ in the range of $10^{-6}$ to 0.25 allows that the flow rate applied to the measuring channel is matched to the specific sensor system employed for detecting a particle. Thereby a specific sensor can be used so that a microfluidic particle analysis device is provided that allows that particles are efficiently detected and that drinking water can be monitored for bacterial content. For example, when $X_{measuring}$ is in the range of $10^{-6}$ to 0.05, e.g. in the range of $10^{-4}$ to 0.01. the microfluidic particle analysis device can employ a sensor using electrical impedance spectroscopy (EIS), since this range of $X_{measuring}$ values will generally allow the flow rates in the measuring channel to match the required flow rate for an EIS sensor.

The microfluidic particle analysis device of the invention can be said to define three general flow directions: a main flow direction of the main channel, a bypass flow direction of the bypass channel, and a measuring flow direction of the measuring channel. The three general flow directions may in particular be defined at or near the inlet manifold so that the main flow direction is the direction of the flowing liquid in the main channel upstream of the inlet manifold, and the bypass flow direction and the measuring flow direction are downstream of the inlet manifold in the respective channels. The flow directions may also be described with vectors so that angles can be defined between the flow directions and/or between the flow directions and the channels. The present inventors have now surprisingly found that if the angle between the main flow direction and the measuring flow direction, e.g. as defined by the measuring channel, is above 60° for a system otherwise as defined above the measuring channel, in particular the entrance of the measuring channel, will be clogged by bacteria after only three days of applying a total flow of drinking water of 30 µl/min through the system. However, if the particle stream is applied to the microfluidic particle analysis device of the invention no clogging of the measuring channel or the inlet of the measuring channel is observed, even after more than 8 days of observation.

Similar observations were found when the angle between the bypass channel, e.g. the bypass flow direction, and the main flow direction is above 60°; undesirable depositions of particles in the inlet flow manifold took place when a flow of liquid was applied for an extended period of time, e.g. three days or more. In contrast, when the angle of the bypass channel relative to the main flow direction is below 60° no deposition of particles occurred. Deposition of bacteria in the inlet manifold may lead to false positive detection results since the bacteria may not be stably deposited and minor fluctuations in the flow of liquid can push the bacteria into the measuring channel, and furthermore deposited bacteria may grow in the inlet manifold, which may also lead to false positive detections, especially for operation over extended periods of time. Thus, the angle of the bypass channel, e.g. the bypass flow direction, relative to the main flow direction is in the range of 0° to 60°.

The present invention thus provides a microfluidic particle analysis device that allows long term, e.g. for more than 3 days, continuous monitoring of drinking water. It is especially noted that if the inlet to the measuring channel or the measuring channel is clogged by bacteria when monitoring drinking water the sensor system for detecting a particle will give a false negative result, and if particles are deposited in the inlet manifold this may lead to false positive results. These problems do not apply with the microfluidic particle analysis device of the present invention.

Without being bound by any particular theory the present inventors believe that the non-Stokes flow when the Reynolds number approach 1, and thus the inertia of the water, will promote deposition of the particles and they have found that the above effects are particularly relevant during sudden directional changes of the flow, i.e. splitting the measuring channel from the bypass channel, particularly when the angle of the measuring channel relative to the main flow direction is above 60 degrees as well as when the angle of the bypass channel relative to the main flow direction is above 60 degrees.

In an embodiment of the invention the measuring channel defines an entry plane in the cross-section of the main channel, which entry plane is orthogonal to the main flow direction. Since the entry plane is orthogonal to the main flow direction the particles in the liquid flowing in the main channel can enter the measuring channel without impinging on any wall, especially since the angle of the measuring channel relative to the main flow direction is less than 60 degrees. Likewise, particles entering the bypass channel can also enter the bypass channel without impinging any walls. Thus, when the microfluidic particle analysis device has a measuring channel defining the entry plane in the cross-section of the main channel the risk of clogging of the inlet of the measuring channel and/or deposition of particles in the inlet manifold is minimised. In general, this embodiment allows that the angle of the measuring channel relative to the main flow direction is 0°. The entry plane will generally be present in a section of the cross-section of the main channel, since the dimensions of the measuring channel will be smaller than the dimensions of the main channel. The angle of the measuring channel relative to the main flow direction may also be larger than 0° when the measuring channel defines the orthogonal entry plane in the cross-section of the main channel.

In a specific embodiment the angle between the measuring channel and the bypass channel is in the range of 0° to 60°. For example, the measuring channel and the bypass channel may be defined in a main channel with a wall parallel to the flow direction of the main channel thus providing an angle of 0°. In a further embodiment the angle between the measuring channel and the bypass channel is in the range of 0° to 60°, e.g. between 0° and 45°, such as 30°, and the measuring channel defines an entry plane in the cross-section of the main channel, which entry plane is orthogonal to the main flow direction.

The sensor system for detecting a particle may be any sensor system capable of detecting a particle. The particle may be any microparticle. In particular, the particle has a size in the range of from 0.1 μm to 10 μm, such as 0.5 μm to 5 μm. The particles may be biological cells, such as prokaryotic cells, e.g. bacteria, or eukaryotic cells, e.g. yeasts, protozoans, parasites, amoebae, plant cells, e.g. algae, or mammalian cells, e.g. blood cells. Other relevant particles may be rust particles or other particles occurring from corrosion. The sensor system will generally have a defined detection limit so that when the concentration of particles surpasses the detection limit the sensor system may give an alarm. The detection limit can be set freely as required by the specific use of the sensor system, but it will depend on the liquid to be monitored and the particles suspected of being contained in the liquid. For example, for purified water (PW) the detection limit may be in the range of 1 ml$^{-1}$ to 100 ml$^{-1}$ or lower, e.g. 10 ml$^{-1}$. For drinking water, depending on the source of drinking water and possible contaminations, the detection limit may also be higher, e.g. in the range of 1,000 ml$^{-1}$ to 10$^7$ ml$^{-1}$, such as 10,000 ml$^{-1}$ to 1,000,000 ml$^{-1}$. The sensor system may also monitor particles in a liquid sample, e.g. the concentration of particles in a liquid sample.

The microfluidic particle analysis device is contained in a substrate, and any appropriate substrate material may be employed. The channels can be formed in the substrate using any technology appropriate for the specific substrate. For example, the substrate may be silicon, e.g. a silicon wafer, and the channels can be formed using lithographic or etching techniques. Lithographic or etching techniques may be used to prepare channels of the same height, but it is also possible to fabricate measuring and bypass channels with different heights. For example, if an isotropic or anisotropic etch is used the height of the bypass channel can be varied throughout the design to change the hydrodynamic resistance of the bypass channel. In an embodiment, a design can be made in which the bypass channel is deeper than the measuring channel by combining e.g. hydrofluoric acid (HF) etch of the bypass channel in glass and patterning of the measuring channels in a dry-film resist. The substrate may also be a polymeric material, and the channels may be formed using, e.g. micromaching, micromoulding, microinjection moulding, laser ablation, 3D printing etc. Lithographic or etching techniques allow much lower tolerances than macrofabrication resulting in each design being identical and thus practically eases any large-scale manufacturing of the resulting product tremendously. Thus, in a specific embodiment the features in the microfluidic particle analysis device, e.g. the width and the height of the channels, have tolerances of about ±1 μm, e.g. about ±0.5 μm. These tolerances are reflected in the value of $X_{measuring}$ so that the concentration of particles of a liquid entering the system is determined more accurately than in a system with higher tolerances.

Systems, especially flow systems, for detection of microparticles will generally have channels of sizes in the same order of magnitude as the particles to be detected in the systems, e.g. with a cross-sectional dimension in the range of from 1 μm to 50 μm. Such a channel will have a hydrodynamic resistance, and the concept of hydrodynamic resistance may be considered an analogue to the electrokinetic law between voltage potential and current, Ohm's law, so that the flow rate, Q, in a channel is related to the applied pressure drop across the channel, ΔP, and hydrodynamic resistance, R, in the following manner: ΔP=R·Q. Microfluidic channels are of small dimensions, e.g. <1 mm, and thus will always have significant hydrodynamic resistances. For a microchannel of rectangular cross-section the hydrodynamic resistance can be approximated using Equation 1:

$$R \cong \frac{12\,\mu L}{wh^3\left(1 - \frac{0.630h}{w}\right)} \quad \text{Equation 1}$$

where μ is the dynamic viscosity, L is the length of the channel, w is the width of the channel, and h is the height of the channel. Equation 1 is valid when h<w but may also be used to approximate the hydrodynamic resistance when h≈w. However, a better approximation of the hydrodynamic resistance when h≈w can be obtained using Equation 2:

$$R \cong \frac{28.4\,\mu L}{h^4} \quad \text{Equation 2}$$

Throughout this document the term "height" is used to describe the cross-sectional dimension of a structure, e.g. a channel, perpendicular to the plane defined by the width and the length of the structure. However, the height may also be referred to as a "depth" and the two terms may be used interchangeably. Calculations for the approximation of hydrodynamic resistances are well-known to the skilled person as shown for example by Theoretical Microfluidics (Henrik Bruus, 2007, Oxford Master Series in Physics 18, Oxford University Press, ISBN 978-0-19-923508-7), the contents of which are hereby incorporated by reference; in particular chapters 1, 2, 3, 4 and 6.

The large hydrodynamic resistance of a microfluidic system is an issue for external pressure-inducing components, e.g. for applying a flow through the microfluidic system. Due to the hydrodynamic resistance, a single microfluidic channel can require 1 to 50 bar of differential pressure to obtain the desired flow rate in the channel. For example, a single channel with cross-sectional dimensions of 10 μm×10 μm and a length of 2 cm has a pressure drop of 9.2 bar at a flow rate of 2 μl/min. For applications which feature continuous operation, a pressure requirement of more than 5 bar limits the choice of pressure-inducing units. This is especially relevant for pumps that dispense volumes in the order of μl/min to ml/min, as very expensive products will function at high back-pressures, but are not relevant for mass production due to cost. This problem thus becomes even more relevant in the context of analysis of media such as drinking water, where it is desirable to monitor large volumes, e.g. thousands of cubic meters. In terms of the present invention "monitoring" does not require that the total volume of the liquid to be monitored is passed through the microfluidic particle analysis device, and analysis of a fraction of the total volume is considered to give a representative result for the total volume of liquid. For a microfluidic device containing an electronic sensor and corresponding electronic components it becomes problematic to integrate all the electronic components in the device, e.g. on the silicon chip, so that longer channels are required than what seems necessary from the dimensions of the component. However, since the microfluidic particle analysis device of the present invention employs a bypass channel it is possible to use a shorter measuring channel compared to a microfluidic device not having the bypass channel. This advantage is particularly relevant when the microfluidic particle analysis device uses an EIS sensor.

Moreover, for channels in this scale, e.g. having cross-sectional dimensions of about 1 mm or less, liquids flowing in the channels are limited to flowing in the laminar regime as may be seen from a calculation of the Reynolds number. The laminar flow means that a liquid flowing in a microchannel will be under "no-slip" conditions where the linear velocity of the liquid at the wall of the microchannel will be zero. No-slip conditions are especially challenging for the analysis of particles present in the flow since the no-slip conditions may result in an inhomogeneous flux distribution of the particles over the cross-section of a microchannel. For the analysis of particles present in low concentrations, e.g. in the detection of bacteria in drinking water or in Purified Water (PW), an inhomogeneous distribution of the bacteria may result in false negative results.

The present inventors have now surprisingly found that despite the no-slip boundary conditions the microfluidic particle analysis device of the invention allows the detection of particles in the measuring channel when a liquid comprising particles is applied to the inlet of the microfluidic particle analysis device. Thus, for example a microfluidic particle analysis device of the invention was designed, which comprised a central bypass-channel from which, at an inlet manifold, two measuring channels split off (see FIG. 1). The channel sizes were varied in order for the measuring channels to each have target $X_{measuring}$ values in the range of 2% to 20%, and flows containing 2 μm polystyrene beads were applied to the microfluidic particle analysis device, and the particles were measured in the measuring channel. The measurements are summarised in Table 1.

TABLE 1

Experimentally recorded flow distribution vs. target $X_{measuring}$ values

| Target $X_{measuring}$ | Target flow in bypass channel | Recorded $X_{measuring}$ |
|---|---|---|
| 2% | 96% | 2.57% |
| 5% | 90% | 6.90% |
| 10% | 80% | 13.92% |
| 20% | 60% | 25.46% |

The results summarised in Table 1 are illustrated in FIG. 8, and as can be seen from FIG. 8 the microfluidic particle analysis device provided consistent results over the analysed system flow rates of up to 2.0 μl/min.

The microfluidic particle analysis device comprises an inlet in fluid communication with an inlet manifold via a main channel. The inlet may have any design allowing connection to an external supply of liquid for analysis. For example, the inlet may comprise a tubular connection having an inner diameter in the range of 100 μm to 1000 μm, e.g. 500 μm or 250 μm. The inlet may also comprise a device for creating a flow of liquid in the microfluidic particle analysis device, such as a pump. If the microfluidic particle analysis device comprises a pump any type of pump may be used, and in particular the pump can provide a liquid flow in the range of 10 μl/min to 1000 ml/min, e.g. 100 μl/min to 1 ml/min, or 1 ml/min to 10 ml/min. In general, the linear flow velocity in the measuring channel will be in the range of 1 mm/s to 1000 mm/s. In a specific embodiment, an external circumventing section is employed where a flow of 150 ml/min is diverted so that 30 μl/min enters the microfluidic particle analysis device and the rest is diverted through the external circumventing section.

In another embodiment the external components comprise a filtering unit for removing particles larger than a cut-off value. The cut-off value may be selected based on the purpose of the microfluidic particle analysis device, e.g. with respect to the size of particles for analysis, so that particles above the cut-off value are removed from the liquid prior to entry into the microfluidic particle analysis device. For example, the filtering unit may have a cut-off value in the range of 2 μm to 20 μm, e.g. 5 μm or 10 μm.

The microfluidic particle analysis device has an inlet manifold providing parallel fluid communication with the bypass channel and the measuring channel. The section from the inlet of the microfluidic particle analysis device to the inlet manifold is referred to as the "main channel". In its simplest form the "inlet manifold" is the location where the measuring channel splits off from the main channel. In a specific embodiment, the bypass channel and the measuring channel, and optionally also the main channel, are laid out in a planar design. In the context of the invention channels in a "planar design" are not limited to being of the same height, i.e. the cross-sectional dimension perpendicular to the plane; the microfluidic particle analysis device may have channels of different heights, which are still considered to be in the same plane.

In a specific embodiment measuring channel splits off from the main channel at an angle between the main channel and the measuring channel in the range of from 135° to 175°, i.e. the angle of the measuring channel relative to the main flow direction is in the range of 5° to 45°. The inlet manifold may comprise a flow guiding structure in upstream fluid communication with the measuring channel. The flow guiding structure comprises an opening to the main channel, which is of a larger cross-sectional area than the measuring channel, and the flow guiding structure has a length of from 2 to 10 times the width of the measuring channel, over which length the flow guiding structure narrows to the width, and optionally the height of the measuring channel if the measuring channel and the main channel are of different heights. Thus, flow guiding structure can be considered to have a funnel shape with the broad end facing the inlet manifold and the narrow end facing the measuring channel. In a specific embodiment the flow guiding structure has the same height as the measuring channel. The flow guiding structure improves the flow conditions as the flow velocity up towards the measuring channel is lowered dramatically. As a result of the lowered the flow velocity the Reynolds number is decreased locally which results in the inertial contribution of the Navier-Stokes equation becoming insignificant. As the inertial forces become insignificant the flow becomes creep flow and thus fewer particles are impinged on the channel walls reducing measuring channel inlet sedimentation. The creep flow also ensures that the concentration of particles in the measuring channel will be closer to the concentration of particles in the liquid applied to the microfluidic particle analysis device.

In an embodiment the main channel is in fluid communication with the inlet via a channel at an angle to the plane of the planar design, e.g. the inlet manifold or the main channel is in fluid communication with the inlet via a channel, which is orthogonal to the plane of the planar design. Thus, the liquid to be analysed in the microfluidic particle analysis device is applied at an angle, e.g. orthogonally, to the planar design of the channels in the microfluidic particle analysis device. Having the inlet at an angle to the plane of the planar design generally simplifies connection of the microfluidic particle analysis device to external components, such as pumps or tubes. Likewise, manufacture the microfluidic particle analysis device is simplified in this embodiment.

In another embodiment the inlet is in plane with the planar design of the measuring channel and the bypass channel. Application of the liquid to be analysed in plane with the planar design of the microfluidic particle analysis device is advantageous since it can minimise deposition of particles prior to the liquid's entry into the inlet manifold. For example, when the inlet is orthogonal to the plane of the microfluidic particle analysis device particles may be deposited where the inlet meets the main channel or the inlet manifold, however, this is prevented when the inlet is in plane with the planar design so that "inlet sedimentation" is prevented.

In a specific embodiment the microfluidic particle analysis device comprises a flow distribution device downstream of the inlet for receiving a flow of liquid from the inlet. The inlet may be at an angle, e.g. orthogonal, to a plane housing the flow distribution device, and the flow distribution device comprises from 2 to 8 collection channels positioned around an inlet point, e.g. positioned symmetrically around the inlet point, with each collection channel being in fluid communication with the main channel, e.g. at a collection point in the main channel. It is preferred that each collection channel has the same hydrodynamic resistance from the inlet point to the collection point. The flow distribution device will minimise the risk that particles in a liquid to be analysed in the microfluidic particle analysis sediment in the interface between the inlet and the main channel or the inlet manifold, e.g. the flow distribution device reduces inlet sedimentation.

Reduction of inlet sedimentation is particularly important for devices for continuous detection of bacteria, as stationary bacteria can grow where sedimented and thus influence the concentration measurements in the device and provide false positive results. Furthermore, when external components comprise flow sections of larger cross-sectional areas than the bypass channel the linear flow velocity in the external section is decreased compared to the linear flow velocity in the microfluidic particle analysis device, and the decreased linear flow velocity may create spaces where particles can settle to that their entry into the microfluidic particle analysis device is delayed or even hindered.

The microfluidic particle analysis device comprises an outlet in fluid communication with the bypass channel and the measuring channel. The main function of the outlet is thus to provide an outlet for the liquid in the microfluidic particle analysis device, and the outlet is not particularly limited. For example, the microfluidic particle analysis device is not limited to a single outlet. In a certain embodiment the bypass channel and the measuring channel are in fluid communication with an outlet manifold where the flows are joined before leaving the microfluidic particle analysis device. The inlet and the outlet may be identical with respect so that the microfluidic particle analysis device can be described as "symmetrical" with respect to the flow through the system and the "inlet" may be used as an "outlet", and vice versa. This ensures that operation at reverse flow can be applied to the device in order to remove particles that may have deposited in the system. For example, after operation during an extended period of time, e.g. more than 3 days, such as at intervals of 5 to 10 days, the flow is briefly reversed before re-establishing the flow in the original direction. The flow may also be reversed more frequently, which may increase the life time of the microfluidic particle analysis device since any build-up of particles can be prevented.

The hydrodynamic resistances of the measuring channel and the bypass channel are calculated from the inlet manifold to the outlet manifold, if present, or at any location where the fluid flows of the measuring channel and the bypass channel meet. It is preferred that the outlet comprises a device for connecting to external components, such as additional tubes, an auxiliary pump or the like. It is further preferred that the hydrodynamic resistance of the outlet, the optional outlet manifold and any external components is insignificant compared to the hydrodynamic resistance of the measuring channel.

The bypass channel and the measuring channel are defined by the flow distribution parameter and thereby by the ratio between their hydrodynamic resistances. The hydrodynamic resistances of the bypass channel and the measuring channel are generally controlled by the cross-sectional area and length of the channels. The bypass channel and the measuring channel may have cross-sectional areas of any shape but the cross-sectional areas are preferably rectangular. For example, the bypass channel may have a width of up to about 1500 µm, e.g. up to about 1000 µm, such as up to about 500 µm. The measuring channel may have a cross-sectional dimension within an order of magnitude of the size a particle to be detected in the microfluidic particle analysis device, and in a preferred embodiment the measuring channel is rectangular and has a cross-sectional dimension in the range of from 1 µm to 50 µm, e.g. the measuring channel has a first cross-sectional dimension in the range of from 5 µm to 20 µm and a second cross-sectional dimension in the range of from 5 µm to 20 µm. In specific embodiments the measuring channel is rectangular with dimensions of 10 µm×10 µm or 10 µm×5 µm.

The microfluidic particle analysis device may have any number of measuring channels, but it is preferred that the microfluidic particle analysis device has a single bypass channel. For example, the microfluidic particle analysis device may have 1 or 2 measuring channels. When the microfluidic particle analysis device comprises 2 or more measuring channels a hydrodynamic resistance may be defined for each measuring channel, and each measuring channel may have the same or different hydrodynamic resistances, and likewise a flow distribution parameter may be defined for each measuring channel. For example, the hydrodynamic resistance of measuring channel n is denoted $R_{measuring,n}$ and the hydrodynamic resistance of the microfluidic particle analysis device, calculated as described above, e.g. from the inlet manifold, is: $(\Sigma_n R_{measuring,n}^{-1} + R_{bypass}^{-1})^{-1}$, and the flow distribution parameter for measuring channel n is correspondingly: $R_{measuring,n}^{-1}$ $(\Sigma_n R_{measuring,n}^{-1} + R_{bypass}^{-1})^{-1}$. The overall hydrodynamic resistance of the microfluidic particle analysis device will also take into account the hydrodynamic resistances of the main channel and other parts, which are added, since the parts are coupled serially. When the microfluidic particle analysis device has two or more measuring channels having different flow distribution parameters the difference in flow distribution parameters improves the quality of the measurement. It is preferred that when the microfluidic particle analysis device has two or more measuring channels the flow distribution parameter is the same for each measuring channel.

In a specific embodiment the microfluidic particle analysis device has two or more measuring channels where a first measuring channel, via a first inlet manifold, is split off from the main channel upstream of a second inlet manifold where a second measuring channel is split off from the bypass channel so that there is a distance between the first and the second inlet manifold. In this embodiment there will be a distance between the entrance to the first and the second measuring channel so that a detection event in the second measuring channel will be delayed compared to the corresponding detection event in the first measuring channel. This embodiment provides a data output of higher quality than embodiments having only a single measuring channel or where two or more measuring channels employ the same inlet manifold. For example, false positive detection results can be minimised.

It is preferred that the overall hydrodynamic resistance of the microfluidic particle analysis device is as low as possible. Thus, in a preferred embodiment the measuring channel has a length corresponding to the minimal length required for housing the sensor system for detecting a particle. For example, the length of the measuring channel may be in the range from 10 µm to 5000 µm, e.g. 100 µm to 2000 µm, such as 1000 µm, or 20 µm to 500 µm. The cross-sectional area of the bypass channel may be equal to or larger than the cross-sectional area of external components, e.g. tubes, connected to the inlet and/or the outlet so that the hydrodynamic resistance per length of the bypass channel is also equal to or less than the hydrodynamic resistance per length of the external tubes. It is preferred that the cross-sectional areas of external components and the bypass channel and/or the main channel are approximately equal. For example, the bypass channel may have a first cross-sectional dimension in the range of from 50 µm to 300 µm and a second cross-sectional dimension in the range of from 50 µm to 300 µm. In a certain embodiment the dimensions of the bypass channel are 200 µm×200 µm. When the cross-sectional areas of the bypass channel and/or the main channel is equal to the cross-sectional areas of the external tubes, the linear velocity of liquid applied in the microfluidic particle analysis device will be equal to the linear velocity of fluid in the external tubes, and thereby sedimentation of particles before entry into the microfluidic particle analysis device is minimised, which is particularly advantageous for a flow system for the detection of particles in a liquid as described above.

In a specific embodiment the measuring channel and the bypass channel have a cross-sectional dimension, e.g. the height, in the range of from 5 µm to 100 µm, e.g. from 5 µm to 50 µm such as from 10 µm to 30 µm; for example the two channels have the same height, e.g. 10 µm. In general, all channels in the microfluidic particle analysis device may have the same height. In this embodiment the ratio of the hydrodynamic resistance per length of the measuring channel to the hydrodynamic resistance per length of the bypass channel is typically in the range of 50 to 500. The bypass channel in this embodiment may have a second cross-sectional dimension, e.g. the width, in the range of 200 µm to 1000 µm.

In a certain embodiment the measuring channel and the bypass channel have a height in the range of 5 µm to 30 µm, the measuring channel has a width in the range of 5 µm to 15 µm, and the bypass channel has a width in the range of 200 µm to 1000 µm. In a specific embodiment the measuring channel and the bypass channel have a height of about 10 µm, the measuring channel has a width of about 10 µm, and the bypass channel has a width of about 500 µm. It this embodiment it is further preferred that the length of the measuring channel is in the range of 1000 µm to 2500 µm, e.g. about 2000 µm, and that the length of the bypass channel is in the range of 1000 µm to 2500 µm, e.g. about 2000 µm, so that $X_{measuring}$ is in the range of about 0.003 to 0.02.

In another embodiment the measuring channel has cross-sectional dimensions of about 5 µm×about 5 µm and the bypass channel has cross-sectional dimensions of about 300 µm×about 300 µm. When the length of the bypass channel in this embodiment is about 10 times the length of the measuring channel $X_{measuring}$ will be about $10^{-6}$; when the length of the bypass channel in is about 100 times the length of the measuring channel $X_{measuring}$ will be about $10^{-5}$.

In yet a further embodiment the measuring channel has cross-sectional dimensions of about 10 µm×about 10 µm and the bypass channel has cross-sectional dimensions of about 100 µm×about 100 µm. When the length of the bypass channel in this embodiment is about 10 times the length of the measuring channel $X_{measuring}$ will be about 0.001; when the length of the bypass channel in is about the same length as the measuring channel $X_{measuring}$ will be about $10^{-4}$.

In other embodiments the length of the measuring channel may be longer than the minimum length required to house the sensor system for detecting a particle. For example, the measuring channel may have a length of up to 3000 µm, e.g. up to 2000 µm or up to 1500 µm. In particular, the measuring channel may contain further sensor systems, so that the length of the measuring channel may reflect this.

The main channel is generally of the same size, e.g. of the same cross-sectional dimensions, as the bypass channel, although the main channel may also have smaller or larger cross-sectional dimensions than the bypass channel.

The heights of the measuring channel, the bypass channel, and the main channel, may be the same, although it is preferred that the height of the measuring channel is lower than the height of the bypass channel and/or the main channel.

In a specific embodiment, the hydrodynamic resistance of the bypass channel may be fine tuned by increasing the length of the bypass channel. As indicated in Equation 1 or in Equation 2 the parameters determining the hydrodynamic resistance of a rectangular channel are primarily the height, especially, and the width, and fine-tuning of the hydrodynamic resistance can be done by controlling the length of the bypass channel. When a bypass channel is desired to be much longer than the measuring channel the bypass channel may take the form of a meander or it may have a spiraling pattern. In a preferred embodiment the measuring channel has cross-sectional dimensions of 10 µm×10 µm, and the bypass channel has cross-sectional dimensions of 200 µm×200 µm. In this embodiment the hydrodynamic resistance per length of channel of the measuring channel is approximately $1.6 \cdot 10^5$ times the hydrodynamic resistance per length of the bypass channel, e.g. when the hydrodynamic resistance is calculated using Equation 2. The ratio of the hydrodynamic resistance per length of channel of the measuring channel to the hydrodynamic resistance per length of the bypass channel is generally in the range of from 1 to 100,000. For certain embodiments the ratio of the hydrodynamic resistance per length of channel of the measuring channel to the hydrodynamic resistance per length of the bypass channel is in the range of from 1000 to 100,000 or more, e.g. up to about 1,000,000. When the depth of the bypass channel is much larger, e.g. in the range of 100 µm to 200 µm, than the depth of the measuring channel, e.g. in the range of 5 µm to 20 µm, it is preferred that the ratio of the length of the bypass channel to the length of the measuring channel is in the range of 10 to 1,000, e.g. 100 to 200. For example, when the measuring channel has cross-sectional dimensions of 10 µm×10 µm, and the bypass channel has cross-sectional dimensions of 200 µm×200 µm, and the ratio of the length of the bypass channel to the length of the measuring channel is about 20 to about 400, $X_{measuring}$ is in the range of 0.0001 to 0.0025. A preferred value of $X_{measuring}$ is in the range of $10^{-4}$ to 0.001, e.g. about 0.001, which can be obtained with a bypass channel about 150 to about 170 times longer than the measuring channel, when the measuring channel has cross-sectional dimensions of 10 µm×10 µm, and the bypass channel has cross-sectional dimensions of 200 µm×200 µm. Other combinations of cross-sectional dimensions of the measuring channel and the bypass channel can also provide this value of $X_{measuring}$. For example, in a specific embodiment the bypass channel has a first cross-sectional dimension in the range of from 50 µm to 300 µm and a second cross-sectional dimension in the range of from 50 µm to 300 µm, and the measuring channel has a first cross-sectional dimension in the range of from 5 µm to 20 µm and a second cross-sectional dimension in the range of from 5 µm to 20 µm. Within this range of cross-sectional dimensions of the measuring channel and the bypass channel, it is preferred that the ratio of the length of the bypass channel to the length of the measuring channel is in the range of 10 to 200, e.g. at about 100 or about 150. The ratio of the length of the bypass channel to the length of the measuring channel may also be in the range of 1 to 10.

In an embodiment of the invention the bypass channel has a first cross-sectional dimension in the range of from 50 µm to 300 µm and a second cross-sectional dimension in the range of from 50 µm to 300 µm, and the measuring channel has a first cross-sectional dimension in the range of from 5 µm to 20 µm and a second cross-sectional dimension in the range of from 5 µm to 20 µm. For example, the bypass channel may have cross-sectional dimensions of 200 µm×200 µm and the measuring channel may have cross-sectional dimensions of 10 µm×10 µm. With a measuring channel in this size the Reynolds number will be about 1 or less than 1 under flow conditions, e.g. at appropriate flow velocities, of relevance in the context of the invention. Traditionally in microfluidics the flow is assumed to be Stokes flow. However, when the Reynolds number is in the order of 1 or more than 1 the flow may be referred to as a non-Stokes flow; in a non-Stokes flow inertial forces become relevant, which is important for a flowing liquid containing particles, and in particular when the flow changes direction, e.g. due to a curved channel or a split of the flow into two or more channels. Due to the non-Stokes flow it is particularly advantageous when the microfluidic particle analysis device has a measuring channel defining an entry plane in the cross-section of the main channel, which entry plane is orthogonal to the main flow direction, since the particles, e.g. bacteria, can be lead into the measuring channel without an abrupt change of direction. Thus, a more accurate concentration determination is obtained for this embodiment of the microfluidic particle analysis device. Moreover, inlet clogging in the measuring channel can be minimised further. Furthermore, a special Reynolds number, $R_p$, may also be calculated for particles flowing in a channel according to Equation 3:

$$R_p = Re \times \frac{a^2}{D_h} \qquad \text{Equation 3}$$

where Re is the Reynolds number, a is the particle diameter, and $D_h$ is the hydraulic diameter of the channel. When $R_p$ is in the order of 1 an inertial focusing of particles will be observed so that when the bypass channel has a first cross-sectional dimension in the range of from 50 µm to 300 µm and a second cross-sectional dimension in the range of from 50 µm to 300 µm particles of about 10 µm or more will be inertially focused in the bypass channel so that clogging of the inlet of the measuring channel by large particles is prevented. The microfluidic particle analysis device is intended for monitoring drinking water that can contain particles in this size range, and therefore this inertial focusing of large particles is an advantage when the cross-sectional dimensions of the bypass channel are in the range of 50 µm to 300 µm.

When the cross-sectional dimensions of the bypass channel are at or above 100 µm×100 µm, the bypass channel may have the same approximate cross-sectional area as external tubes commonly used for microfluidic systems, and therefore the overall hydrodynamic resistance of the bypass channel does not significantly increase the overall hydrodynamic resistance of the microfluidic particle analysis device, e.g. compared to the hydrodynamic resistance of external tubes, and the length of the bypass channel can be chosen freely. For example, the ratio of the length of the bypass channel to the length of the measuring channel may be up to 500.

The microfluidic particle analysis device is generally suited for use with a volumetric flow in the range of from 10 µl/min to 10 ml/min applied to the inlet of the microfluidic particle analysis device. For example, when $X_{measuring}$ is in the range of from 0.0001 to 0.001 a suitable volumetric flow rate of the microfluidic particle analysis device is in the range of 100 µl/min to 10 ml/min, e.g. 0.5 ml/min to 5 ml/min. When $X_{measuring}$ is in the range of from 0.001 to 0.25, a suitable volumetric flow rate of the microfluidic particle analysis device is in the range of 10 µl/min to 1 ml/min, e.g. 50 µl/min to 500 µl/min. In a specific example, the measuring channel has cross-sectional dimensions of 10 µm×10 µm, and in this case it is preferred that the volumetric flow rate in the measuring channel is in the range of 0.1 µl/min to 10 µl/min, e.g. 0.5 µl/min to 2 µl/min. The flow rate in the measuring channel may also be expressed as a linear flow velocity, and it is preferred that the linear flow velocity in the measuring channel is in the range of 5 mm/s to 500 mm/s, e.g. 20 mm/s to 300 mm/s, such as 20 mm/s to 100 mm/s. The flow rate in the measuring channel can be calculated from knowledge of $X_{measuring}$ and the total flow rate applied to the microfluidic particle analysis device. The microfluidic particle analysis device is not limited to a volumetric flow in this range, and in other embodiments the volumetric flow may be in the range of 10 ml/min to 100 ml/min.

The microfluidic particle analysis device may further comprise an external circumventing section, e.g. when $X_{measuring}$ is in the range of from $10^{-6}$ to 0.001, e.g. in the range of 0.0001 to 0.001, in particular when the cross-sectional dimensions of the measuring channel are in the range of from 5 µm to 20 µm. An external circumventing section may comprise an inlet branch, e.g. upstream of the inlet of the microfluidic particle analysis device, for dividing a liquid flow into an analysis stream for application to the microfluidic particle analysis device and a circumvention stream that will not enter the microfluidic particle analysis device. For example, when the cross-sectional dimensions of the bypass channel and the main channel are in the range of from 50 µm to 300 µm, the circumventing section, e.g. the tubes of the circumventing section, may have cross-sectional dimensions in the range of from 200 µm to 1,000 µm, e.g. 500 µm to 1000 µm. The cross-sectional area and length of the circumventing section may be chosen to divert a predetermined amount of the flow, e.g. from 80% to 90% or more, into the circumventing section. An external circumventing section may be integrated with a pump and may take the form of a flow-splitter. The external circumventing section allows that the microfluidic particle analysis device is operated at a higher volumetric flow rate, since it allows that a smaller proportion of the liquid for analysis is applied to the microfluidic particle analysis device and thereby the linear flow velocity, in particular in the measuring channel, can be controlled to be in a range desirable for the sensor for detecting a particle.

In an embodiment of the invention the sensor system for detecting a particle employs EIS for detecting particles. EIS in the context of microfluidic systems is reviewed by Cheung et al. 2010 (*Cytometry Part A*, 2010, 77A: 648-666), which is hereby incorporated by reference. Thus, in an embodiment of the invention the microfluidic particle analysis device has a particle detection system comprising a first electrode and a second electrode defining an operating space between the first electrode and the second electrode, which first and second electrodes are in electrical connection via an electric circuit comprising an alternating current (AC) or a direct current (DC) source and a device for monitoring an electrical signal from the first and/or the second electrode. EIS spectroscopy in a flow system, in particular for the detection of bacteria in drinking water, is limited by the fact that cross-sectional dimensions of a channel housing the electrodes are controlled by the size of the particles to be detected. For example, an EIS system for the detection of bacteria should have at least one cross-sectional dimension of about 20 µm or less in a channel housing the EIS electrodes, since EIS electrodes in a larger channel may not detect a bacterium in the channel. The microfluidic particle analysis device of the present invention is particularly advantageous for the analysis of large volumes of liquids, such as drinking water, since the bypass channel allows that large volumes of liquid are applied to the system while allowing that a small fraction, e.g. in the range of $10^{-6}$ to 0.25, e.g. in the range of 0.0001 to 0.01, in particular about 0.001, of the total volumetric flow, is diverted from the liquid flow in the microfluidic particle analysis device for analysis in the measuring channel. This allows that the microfluidic particle analysis device is employed with a total volumetric flow of up to about 10 ml/min, which is suitable for a device for screening drinking water. It is furthermore advantageous that the stream of liquid diverted into the measuring channel has a sufficient proportion of particles from the liquid in order for the particles to be detected, e.g. by EIS. The microfluidic particle analysis device further allows that EIS is employed for the detection of particles without requiring hydrodynamic focusing or without positioning the particles using dielectrophoretic focusing. Thus, in an embodiment of the invention the microfluidic particle analysis device does not employ hydrodynamic focusing. In another embodiment the microfluidic particle analysis device does not employ dielectrophoretic focusing. Neither dielectrophoretic focusing nor hydrodynamic focusing are, however, ruled out, and both principles may be used in the microfluidic particle analysis device.

The first and the second electrode may be on the same wall of the measuring channel, e.g. the first and the second electrode may be in a "coplanar" set-up, or the first and the second electrode may be positioned on opposite walls in the measuring channel, e.g. the first and the second electrode may be in a "parallel overlap" set-up. When the two electrodes are coplanar the operating space is parallel to the direction of the flow in the measuring channel, and the operating space is the distance between the electrodes, i.e. from the edge of the first electrode to the edge of the second electrode. The operating space of coplanar electrodes may be in the range of from 1 µm to 50 µm, e.g. 1 µm to 20 µm. When the two electrodes are in a parallel overlap set-up the operating space is perpendicular to the direction of the flow in the measuring channel, and the operating space is the distance between the opposite walls of the measuring channel, e.g. 1 µm to 50 µm. The first and the second electrode are generally of the same size, e.g. with superficial dimensions in the range of 1 µm to 100 µm, e.g. 5 µm to 50 µm, although the first and the second electrode may also have different sizes. The electrodes may be of any conducting material but are generally metallic, e.g. prepared from titanium, gold, nickel, copper, iridium, platinum, palladium, or combinations and alloys thereof.

The electrodes are in electrical connection via an electric circuit comprising the AC or DC source and a device for monitoring an electrical signal. The electrical circuit may comprise conductors, which are integrated with the microfluidic particle analysis device, in the substrate of the microfluidic particle analysis device. The AC or DC source may be chosen as appropriate, and an AC source may provide frequencies in the kHz to MHz range, e.g. from 100 kHz to 20 MHz. The voltage between the first and the second electrode will typically be in the range of 0.1 V to 10 V, e.g. 0.5 V to 5 V. The device for monitoring an electrical signal may comprise a processing device for analysing a signal recorded from the electrodes. The device for monitoring an electrical signal may further comprise an output device for displaying or transferring data from the device for monitoring the electrical signal. A device for transferring data may operate using any wireless or wired data transmission protocol.

In use a voltage is applied to the first electrode and a current is measured at the second electrode. The first electrode may also be referred to as the "excitation electrode", and the second electrode may also be referred to as the "reference electrode". The measured current is recorded, e.g. continuously at a predetermined sample rate. When a liquid without any particles passes the electrodes, e.g. the operating space, the reference electrode will provide a "base signal", and when a particle, such as a biological cell, e.g. a bacterium, passes the operating space the signal will change.

In a specific embodiment the electrodes are arranged in a coplanar set-up, and the particle detection system comprises an excitation electrode located between two reference electrodes. The measurements electrodes comprise a first reference electrode upstream of the excitation electrode and a second reference electrode downstream of the excitation electrode. In this embodiment the operating space is divided into an onset operating space between the first reference electrode and the excitation electrode and a balance operating space between the excitation electrode and the second reference electrode. In use a voltage is applied to the excitation electrode and a current is measured at the two reference electrodes. A particle passing through the operating space will first encounter the onset operating space where its presence will be recorded by a change in the signal between the excitation electrode and the first reference electrode. When the particle is in the onset operating space no change in the signal will be recorded between the excitation electrode and the second reference electrode, but when the particle reaches the balance operating space its presence will be recorded by a change in the signal between the excitation electrode and the second reference electrode, whereas no change in the signal will be recorded between the excitation electrode and the first reference electrode. This allows that the same particle is recorded twice by the electrode set-up, and thereby the velocity of a particle can be measured. Measurement of the particle velocity allows that the overall flow velocity, e.g. the linear flow velocity, of the liquid in the measuring channel is estimated. Thus, this embodiment allows that the flow rate through the microfluidic particle analysis device is estimated. Knowledge of the fluid velocity in the measuring channel further provides a better estimate of the concentration of particles in the liquid than can be recorded when only a single reference electrode is employed, since the signals can be correlated with the estimated fluid velocity. This same effect can be obtained when the particle detection system comprises two or more sets of electrodes arranged in a parallel overlap set-up, wherein a first, i.e. upstream, set of electrodes define an onset operating space and a second, i.e. downstream set of electrodes define a balance operating space. In both embodiments the size of the onset operating space and the balance operating space may be the same, or the sizes may differ from each other.

In another aspect the invention relates to a method of detecting a particle in a fluid, the method comprising: providing a microfluidic particle analysis device according to the invention, providing a sample fluid suspected of containing a particle having a dimension in the range of from 0.1 μm to 10 μm, applying a flow of the sample fluid from the inlet to the outlet of the microfluidic particle analysis device, detecting a particle in the measuring channel using the sensor system for detecting a particle.

Any microfluidic particle analysis device of the invention may be used in the method, but it is preferred that the microfluidic particle analysis device, as outlined above, comprises a first electrode and a second electrode defining an operating space between the first electrode and the second electrode, which first and second electrodes are in electrical connection via an electric circuit comprising an AC or a DC source and a device for monitoring an electrical signal from the first and/or the second electrode. This embodiment comprises the further steps of applying an AC or DC current from the current source to create an electric field in the operating space, and monitoring a differential electrical signal between the first and the second electrode.

The microfluidic particle analysis device is particularly suited for analysing drinking water, and it is preferred that the sample fluid suspected of containing a particle is drinking water. However, the method is not limited to drinking water and the method may be used to detect a particle in any appropriate liquid. Preferred particles are biological cells as outlined above. In a preferred embodiment, the sample fluid suspected of containing a particle contains particles at a concentration in the range of 0 ml$^{-1}$ to 10$^8$ ml$^{-1}$, e.g. 100 ml$^{-1}$ to 10$^6$ ml$^{-1}$, such as 1000 to 10$^4$ ml$^{-1}$. When the sample fluid suspected of containing a particle is drinking water, the concentration of particles, e.g. bacteria, will typically be in the range of 0 ml$^{-1}$ to 10$^5$ ml$^{-1}$, e.g. 10$^2$ ml$^{-1}$ to 10$^5$ ml$^{-1}$. A concentration of bacteria of 10$^5$ ml$^{-1}$, 10$^4$ ml$^{-1}$, 10$^3$ ml$^{-1}$, 500 ml$^{-1}$, 200 ml$^{-1}$, 100 ml$^{-1}$, 50 ml$^{-1}$, 10 ml$^{-1}$, or 1 ml$^{-1}$ may be set as a detection limit, which, depending on the application, will activate an alarm. The alarm may also be set to take into consideration other parameters, such as the rate of increase in particle concentration. The microfluidic particle analysis device is not limited to analysing drinking water and microfluidic particle analysis device may also be used in e.g. food applications where the monitoring of cells and their concentration is relevant. Exemplary food applications are within the dairy industry and production of alcoholic beverages, e.g. beer, wine, cider, etc. The method of the invention is also relevant with process liquids from fermentations to produce biochemical or biological compounds.

In another aspect, the invention relates to a method of monitoring, e.g. measuring, the concentration of particles in a fluid. The method comprises providing a microfluidic particle analysis device according to the invention, providing a sample fluid containing particles having a dimension in the range of from 0.1 μm to 10 μm, applying a flow of the sample fluid from the inlet to the outlet of the microfluidic particle analysis device, monitoring, e.g. measuring, a concentration of the particles in the measuring channel using the sensor system for detecting a particle. It is preferred that the microfluidic particle analysis device employed in this embodiment comprises a particle detection system for EIS as described above. It is particularly preferred that the particle detection system for EIS comprises electrodes set up to define an onset operating space and a balance operating space as described above. This aspect is particularly suited in fields where process fluids contain particles in the indicated size range. Exemplary particles are microbial cells, e.g. bacteria or yeasts, used in the fermentation of food products, e.g. dairy products or alcoholic beverages, or in fermentations to produce biochemical or biological compounds, e.g. pharmaceutical proteins or peptides, small molecules etc.

In general, the features outlined for the aspect relating to the microfluidic particle analysis device are also relevant for the method aspects of the invention, and vice versa. Any feature described in the context of any aspect may be used in any other aspect in combination with any other feature, and all such combinations are contemplated in the present invention even though the combinations may not be mentioned explicitly. In particular, any feature discussed for the aspect relating to the microfluidic particle analysis device is also relevant for the method aspect of the invention.

BRIEF DESCRIPTION OF THE FIGURES

In the following the invention will be explained in greater detail with the aid of an example and with reference to the schematic drawings, in which.

DETAILED DESCRIPTION OF THE INVENTION

The present invention relates to a microfluidic particle analysis device comprising an inlet in fluid communication via a main channel defining a main flow direction with an inlet manifold providing parallel fluid communication with a bypass channel of hydrodynamic resistance $R_{bypass}$, and a measuring channel of hydrodynamic resistance $R_{measuring}$, the measuring channel having a cross-sectional dimension in the range of from 1 µm to 50 µm and further having a sensor system for detecting a particle, wherein a flow distribution parameter $X_{measuring} = R_{measuring}^{-1}(R_{measuring}^{-1} + R_{bypass}^{-1})^{-1}$ is in the range of from $10^{-6}$ to 0.25, wherein the angle of the measuring channel relative to the main flow direction is in the range of 0° to 60°, and wherein the angle of the bypass channel relative to the main flow direction is in the range of 0° to 60°, and the microfluidic particle analysis device further comprising an outlet in fluid communication with the bypass channel and the measuring channel. In another aspect the invention relates to a method of detecting a particle in a fluid using the microfluidic particle analysis device. In another aspect the invention relates to a method of monitoring the concentration of particles in a fluid using the microfluidic particle analysis device.

Figure 1:
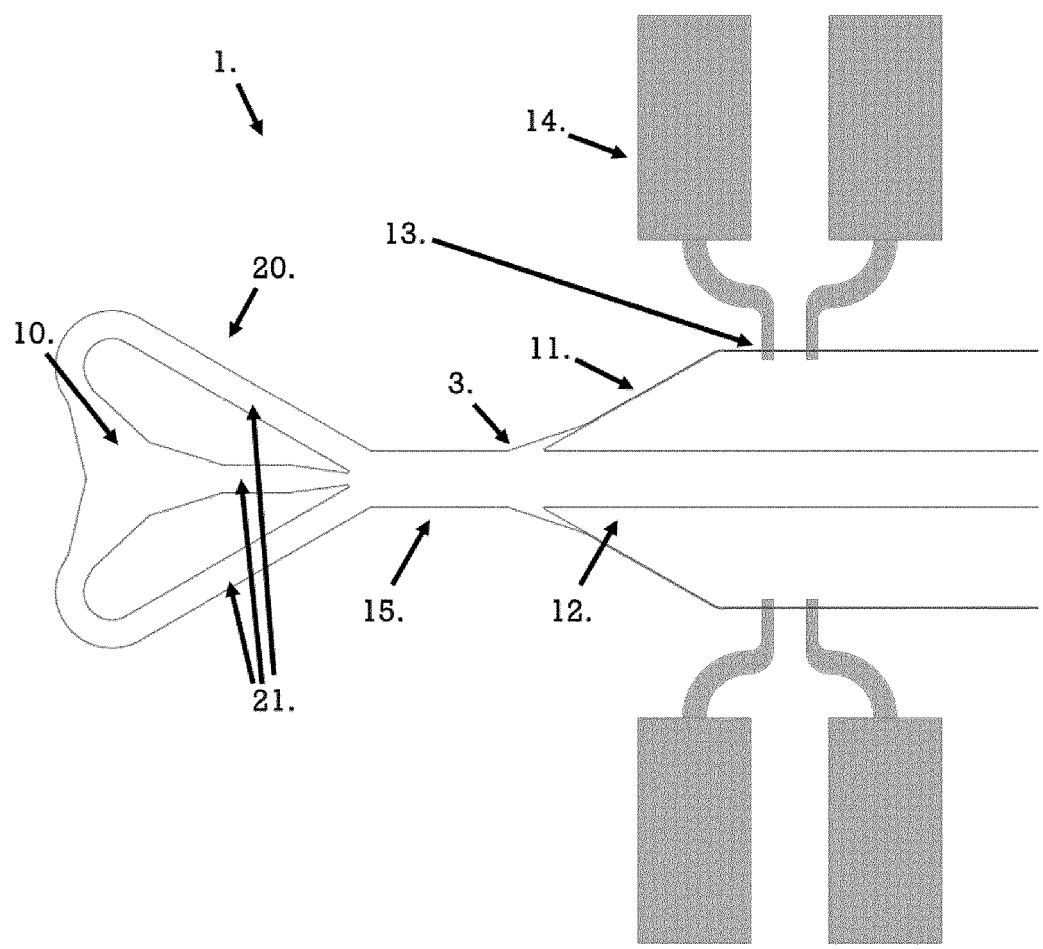
FIG. 1 illustrates a top-view of an embodiment of the invention.
Figure 2A:
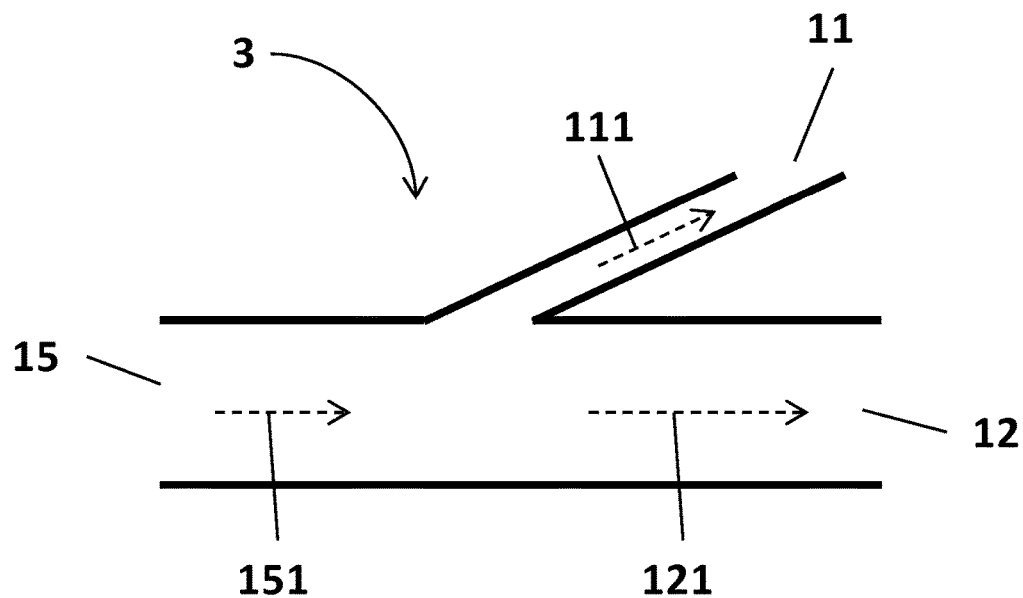
FIG. 2 illustrates details of embodiments of the invention.
Figure 2B:
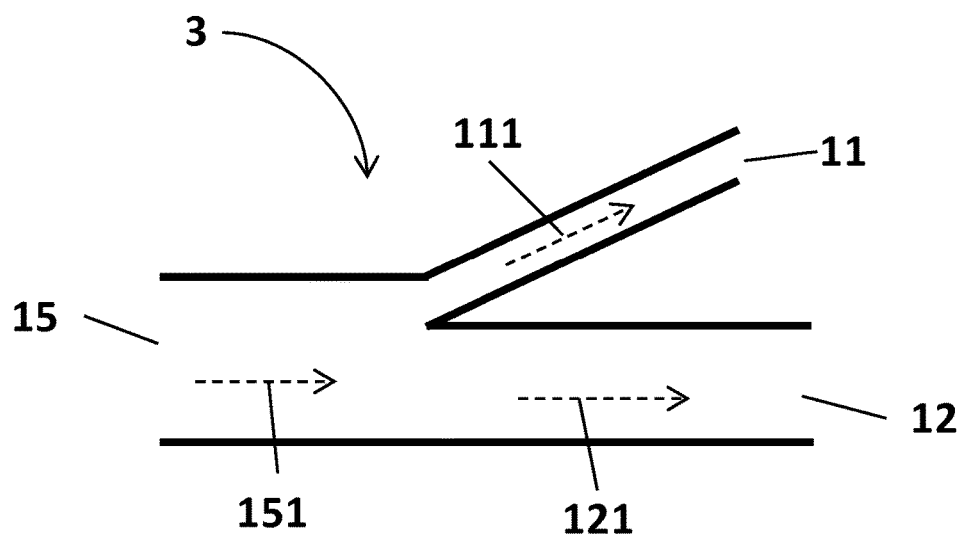
Figure 2C:
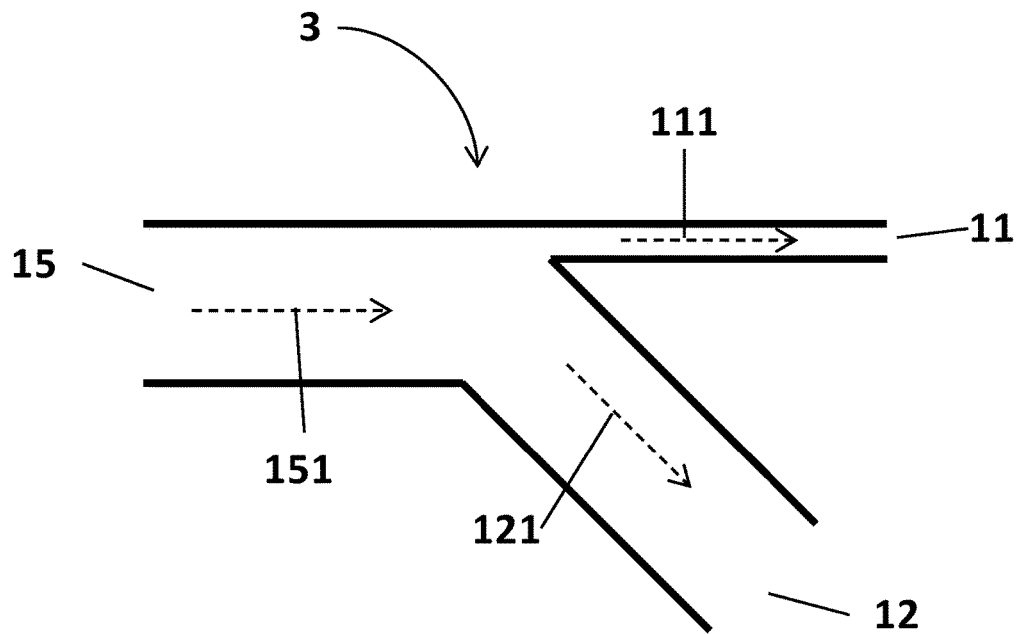
Figure 2D:
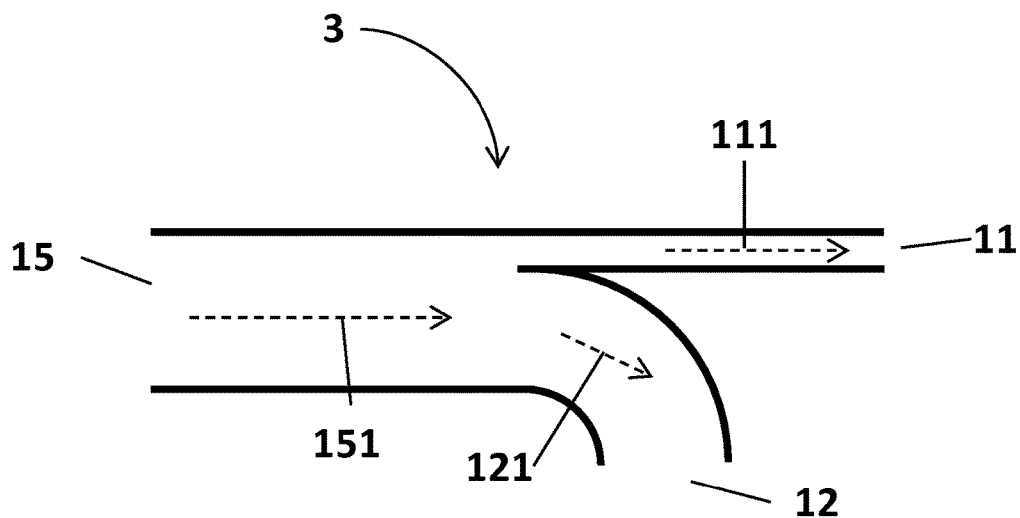

An embodiment of the microfluidic particle analysis device 1 is illustrated in FIG. 1, in which two measuring channels 11 and a bypass channel 12 are in fluid communication with an inlet manifold 3. The microfluidic particle analysis device has a sensor system 13 for detecting a particle, which in the embodiment of FIG. 1 has two electrodes 14 for electrical impedance spectroscopy (EIS).

FIG. 2 shows top views of different embodiments (in panels a to d) of the inlet manifold 3 of the invention. Thus, FIG. 2 illustrates the inlet manifold 3, the main channel 15, the measuring channel 11 and the bypass channel 12; the channels in FIG. 2 are not drawn to scale, e.g. with respect to the cross-sectional dimension of the channels since the figure shows the layout of the channel. FIG. 2 also shows the main flow direction 151 in the main channel 15, the bypass flow direction 121 in the bypass channel 12, and the measuring flow direction 111 in the measuring channel 11. The flow directions are illustrated as vectors, and angles between different channels may e.g. be calculated from the vectors. FIG. 2a shows an embodiment where the measuring channel 11 splits off from the main channel, whereas FIGS. 2b, c and d show embodiments where the measuring channel defines an entry plane in the cross-section of the main channel, which entry plane is orthogonal to the main flow direction.

The microfluidic particle analysis device of the invention is particularly suited for detecting bacteria in drinking water or industrial process water, e.g. Purified Water (PW). Monitoring drinking water will generally comprise continuous monitoring of water from a source, which is distributed to an end user. The drinking water will be of low conductivity, e.g. <1 mS/cm, but the microfluidic particle analysis device may also be used with liquids of higher conductivity, e.g. process streams, such as fermentation broths, milk, beer, wine, etc., or lower conductivity, such as PW, e.g. for pharmaceutical production.

In the context of this invention the term "microfluidic" is intended to cover a range of sizes where the smallest dimension of channels is in the range from about 1 µm to about 1 mm, e.g. about 10 µm to about 200 µm, and in general the channels will not contain constrictions. It can generally be said that fluids in microfluidic fluidic systems will be flowing under laminar conditions, and fluidic systems with channels different from those defined above may well be described as "microfluidic" as long as fluids contained in the systems flow under laminar conditions.

The microfluidic particle analysis device can also be referred to as a flow system. A "flow system", such as the microfluidic particle analysis device of the invention, may be operated continuously. In contrast, certain microfluidic analysis devices are operated in a "batch wise" manner, where one or more samples are added to the system for analysis, but where the system does not allow a continuous flow through the system. A continuous flow is advantageous over batch wise analysis since a positive detection result can be obtained faster than when samples need to be extracted and analysed, e.g. the time between sampling is reduced to zero.

The microfluidic particle analysis device is a flow system where a flow of liquid enters the inlet and leaves the microfluidic particle analysis device via the outlet. Thus, the inlet and the outlet define a direction of the flow in the microfluidic particle analysis device, and in this context elements of the microfluidic particle analysis device may be "upstream" or "downstream" relative to each other with respect to the direction of flow.

The microfluidic particle analysis device may have channels of specific hydrodynamic resistances. The hydrodynamic resistance of a channel is generally determined by the cross-sectional dimensions of the channel and also by its length. However, a channel may also comprise surfaces, which have been treated to modify the hydrodynamic resistance. For example, the surface of a channel, e.g. a measuring channel, may be treated to decrease the hydrodynamic resistance, e.g. by coating the surface or by micro- or nanostructuring the surface.

The microfluidic particle analysis device comprises channels. In the context of the invention a channel may have any cross-sectional shape, e.g. the channel may be square, rectangular, round, etc. It is preferred that the channels, especially the measuring channel, are rectangular. The microfluidic particle analysis device is not limited to channels of the same cross-sectional shape, and the cross-sectional shape of a single channel may vary over the length of the channel.

The microfluidic particle analysis device may comprise a pump, e.g. for pushing liquid through the microfluidic particle analysis device via the inlet, and the microfluidic particle analysis device may also comprise an auxiliary pump, e.g. for aspirating liquid via the outlet. The pump may be any pump appropriate for the specific task, and exemplary pumps are a piston pump, a syringe pump, a peristaltic pump, a membrane pump, a diaphragm pump, a gear pump, a microannular gear pump, or any other appropriate type of pump.

The microfluidic particle analysis device may comprise a filtering unit. A "filtering unit" according to the present invention is to be understood in the broadest terms as a unit capable of separating solids, e.g. particles larger than particles intended for detection or quantification, and liquid. Thus, the filtering unit may be, e.g. a sieve, a packed bed of particles, a filter paper, a filter membrane etc.

Figure 3:
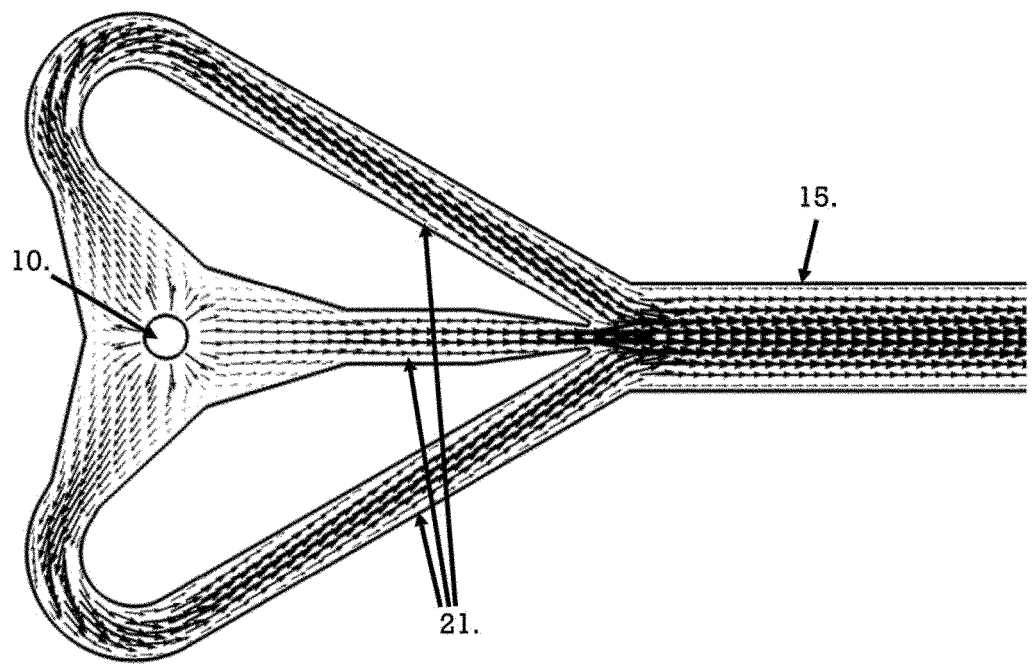
FIG. 3 illustrates a top-view of a flow distribution device in an embodiment of the invention.

In the embodiment illustrated in FIG. 1 and FIG. 3 the microfluidic particle analysis device 1 comprises two measuring channels 11 and a bypass channel 12 arranged in the same plane. The microfluidic particle analysis device 1 has a flow distribution device 20 where the inlet is orthogonal to the plane also housing the flow distribution device 20, which comprises 3 collection channels 21 positioned symmetrically around an inlet point 10, with each collection channel 21 being in fluid communication with the main channel 15. In the microfluidic particle analysis device 1 of FIG. 1 the inlet manifold 3 comprises flow guiding structures in upstream fluid communication with the measuring channels 11.

Figure 4:
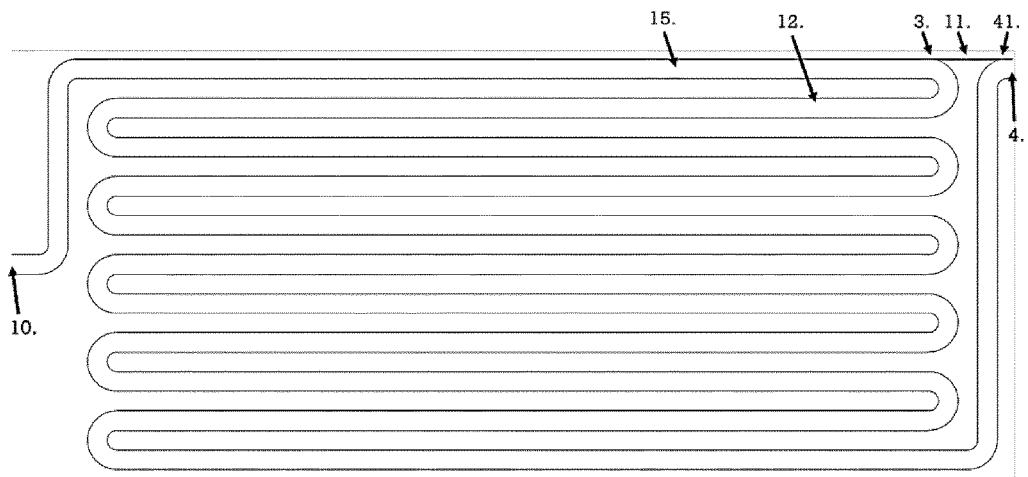
FIG. 4 illustrates a top-view of the channel layout in an embodiment of the invention.

FIG. 4 shows an embodiment where the main channel 15 and the bypass channel 12 are of the same cross-sectional area, e.g. having cross-sectional dimensions of 200 µm×200 µm, and a single measuring channel 11 has cross-sectional dimensions of 10 µm×10 µm. The bypass channel 12 has a meander shape and a length of 160 times the length of the measuring channel 11, so that $X_{measuring}$ is 0.001. The length of the bypass channel can easily be reduced to obtain a smaller $X_{measuring}$ value or increased to obtain a larger $X_{measuring}$ value. Thus, modification of the length of the bypass channel allows fine tuning of $X_{measuring}$ value. FIG. 4 also indicates the inlet point 10 and the outlet 4, as well as the inlet manifold 3 and the outlet manifold 41. The embodiment illustrated in FIG. 4 is employed in the embodiment shown in FIG. 7, which also indicates the inlet 2 and the outlet 4 of the microfluidic particle analysis device 1.

Figure 5:
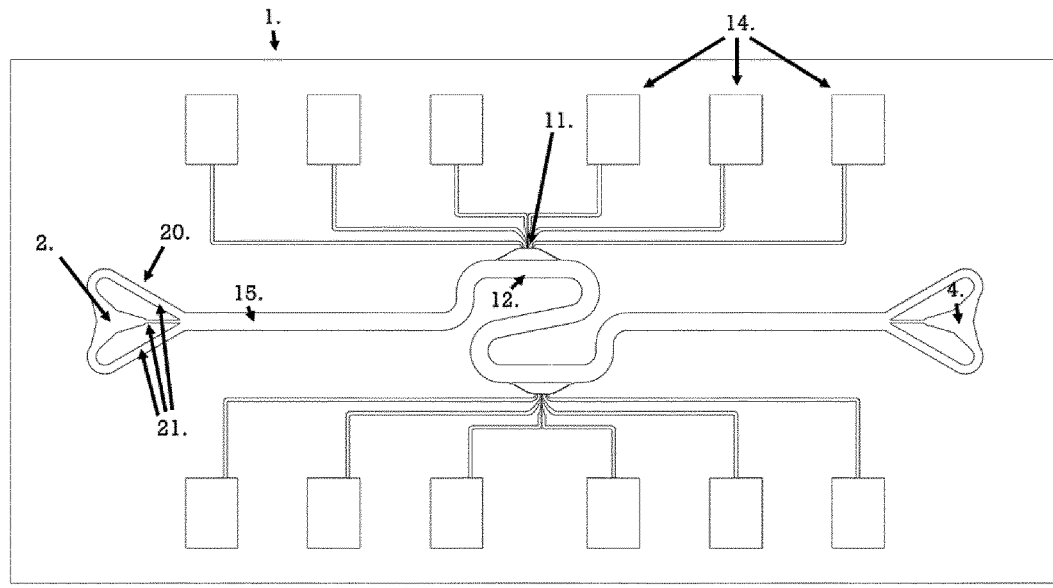
FIG. 5 illustrates a top-view of the channel layout in an embodiment of the invention.

FIG. 5 shows another embodiment of the microfluidic particle analysis device 1 where the main channel 15, the bypass channel 12 and the measuring channel 11 have the same height of 10 µm. The main channel 15 and the bypass channel 12 are of the same cross-sectional area having a width of 500 µm. The width of the measuring channel is 10 µm. The length of the measuring channel is 1920 µm and the length of the bypass channel, e.g. from the inlet manifold to the outlet manifold, is 1800 µm. Thus, $X_{measuring}$ is 0.008. FIG. 5 also indicates the inlet 2 in fluid communication with a flow distribution device 20 having three collection channels 21 positioned symmetrically around an inlet point. A structure similar to the flow distribution device 20 is indicated at the outlet 4. With this structure at the outlet the channel layout is rotationally symmetrical, which simplifies manufacture of the microfluidic particle analysis device and enables reverse flow operation where clogging can also be removed.

Certain embodiments of the invention employ EIS. EIS is generally well-known to the skilled person. Thus for example, Cheung et al. 2010 (*Cytometry Part A*, 2010, 77A: 648-666), describe EIS, in particular in the paragraph Impedance Analysis as a Label-Free and Non-Invasive Technique (p. 649), which is hereby incorporated by reference. Likewise, Houssin et al. (*IEEE SENSORS* 2009 Conference, 396-399), p. 397 in particular; Gawad et al. (*Lab Chip*, 2004, 4: 241-251); Cheung et al. 2005 (*Cytometry Part A*, 2005, 65A:124-132), in particular Impedance Spectroscopy Flow Cytometry, p. 125; and David et al. (*Biotechnology and Bioengineering*, 2011, 109: 483-492), all describe EIS and all are hereby incorporated by reference.

Figure 6:
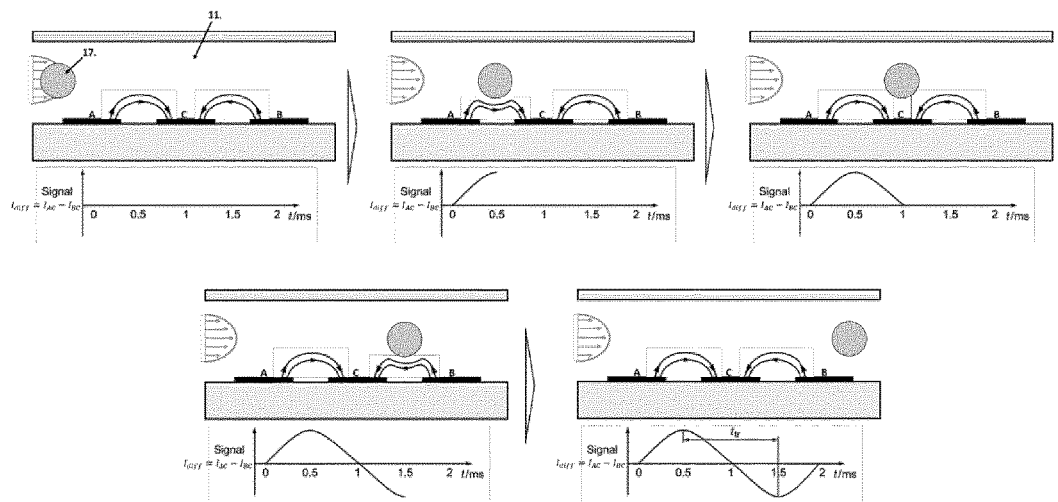
FIG. 6 illustrates the electrode layout of an embodiment of the invention.

In a specific embodiment the electrodes are arranged in a coplanar set-up, and the microfluidic particle analysis device comprises a first excitation electrode located between two reference electrodes as illustrated in FIG. 6. A voltage is applied to the excitation electrode C and a current is measured at the two reference electrodes A,B. The signals from the two reference electrodes are subtracted ($I_{diff}=I_{AC}-I_{BC}$) in order to obtain a characteristic transition signal as illustrated in FIG. 6. When no particle is present between the electrodes the measured current is equal at electrode A and B ($I_{AC}=I_{BC}$), and the differential signal is therefore zero ($I_{diff}=0$). As the particle 17 moves into the volume between the upstream reference electrode A and the excitation electrode C, i.e. the operating space, the signal measured on the upstream reference electrode A changes. The signal on the downstream reference electrode B will, however, not change and the differential current will be different from zero ($I_{diff}\neq0$). The maximum differential current is measured when the particle is positioned exactly between the upstream reference electrode A and the excitation electrode C. When the particle is exactly above the centre of excitation electrode C, the measured signals will again be equal ($I_{diff}=0$). The minimum differential current is measured when the particle is positioned exactly between excitation electrode C and downstream reference electrode B.

The magnitude and shape of the transition signal at several frequencies is used to characterise the particle properties and sample features. Specifically, the transition signal can be used to determine the velocity with which the particle moves across the electrodes, by considering the length the particle has moved and the time of the transition. The time can be determined directly from the transition signal by evaluating the time from the maximum peak to the minimum peak. The distance traveled by the particle is evaluated by considering two things. First of all, the width of the electrodes and the distance between them, which are specific dimensions chosen during the design of the chip and are very well defined. Secondly, due to the microscopic dimensions of the channel, the flow in the channel is laminar. This means that the particle will stay in the same position in the channel during a transition, and will move in a straight line across the electrodes. Thus, by determining the time between the maximum and minimum differential current and the physical distance, s, that the particle has traveled, the exact velocity of the particle can be calculated (see FIG. 6). By evaluating the flow velocity of the particles and using the well defined channel dimensions one can easily determine the flow rate in the measuring channel, as the particles will follow the flow in the measuring channel under any given condition presented within this invention.

Figure 7:
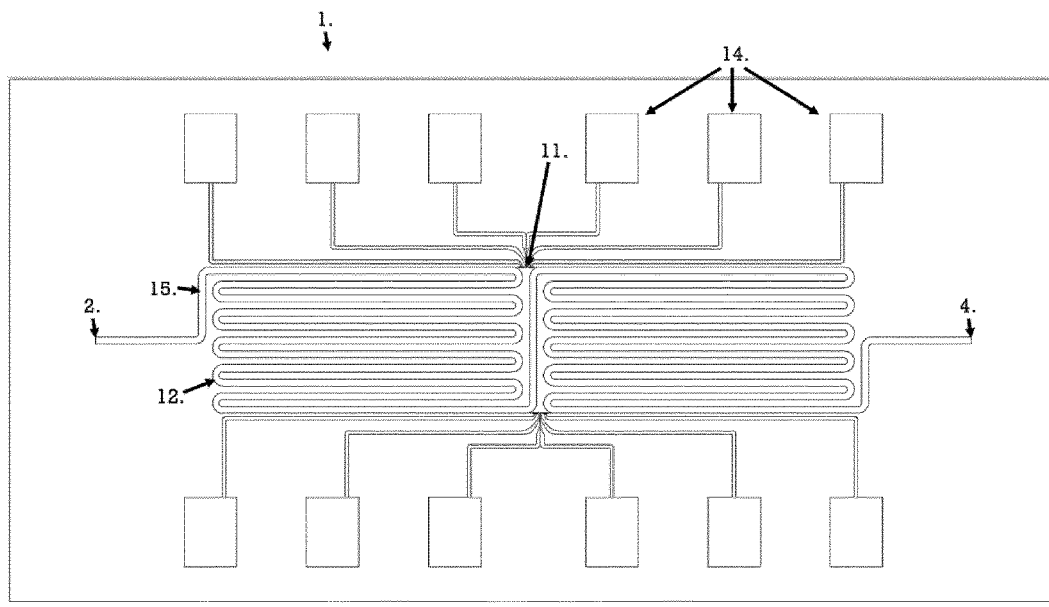
FIG. 7 illustrates a top-view of an embodiment of the invention.

The microfluidic particle analysis device may be fabricated using any appropriate technology, but it preferred that the microfluidic particle analysis device is fabricated using cleanroom facilities due to the small critical dimensions of the measuring channel. The fabrication process may thus involve standard fabrication procedures such as an electrode lift-off process, photolithography and direct bonding, as are well-known to the skilled person. The layouts of two embodiments of the microfluidic particle analysis device are illustrated in FIG. 5 and FIG. 7, respectively. In general the microfluidic particle analysis device 1 comprises an inlet 2 in fluid communication with a main channel 15, which has the same cross-sectional dimensions as the bypass channel 12. The microfluidic particle analysis devices 1 of FIG. 5 and FIG. 7 have a first measuring channel 11 upstream of a second measuring channel. The length of both measuring channels in FIG. 7 is 100 µm. The length of both measuring channels in FIG. 5 is 1930 µm. The width of the bypass channel 12 in FIG. 7 is 200 µm, and the width and height of the measuring channel are 10 µm. The linear distance between the first measuring channel 11 and the second measuring channel is approximately 16,000 µm so that the length of the bypass channel 12 is 160 times the length of the measuring channels, and the linear distance in the bypass channel 12 between the inlet manifold of the second measuring channel and the outlet manifold of the second measuring channel is approximately 16,000 µm. The measuring channels each contain a reference electrode and an excitation electrode, and the length of the electrodes relative to the length of the measuring channels is 25 µm. The widths of the electrodes span the width of the measuring channels. The operating space between the electrodes is 50 µm. In another embodiment, the length of the electrodes relative to the length of the measuring channels is 10 µm. The widths of the electrodes span the width of the measuring channels. The operating space between the electrodes is 10 µm.

In one embodiment, e.g. as illustrated in FIG. 5, the bypass channel 12 and the measuring channel 11 have the same heights, and the channel features are fabricated in an applied photoresist polymer. The microfluidic channels may be enclosed between a bottom and a top substrate, e.g. the top and bottom substrates may be made of borosilicate glass, however silicon or a polymer may also be used as a substrate.

In a first process step electrodes 14 are deposited onto a bottom substrate in order to produce a microfluidic particle analysis device 1 having coplanar electrodes 14, or the electrodes 14 are deposited onto a bottom and a top substrate in order to produce a microfluidic particle analysis device 1 having parallel overlapping electrodes 14. The electrodes 14 can be made using, in a cleanroom, a standard lift-off process with e-beam deposition of the electrode metals, e.g. Ti as adhesive layer and Au or Pt as conductive layer. The total thickness of the electrodes is usually between 100 and 200 nm.

A second process step may involve creation of the inlet and outlet holes (not shown) on the top substrate, e.g. using powder blasting. Powder blasting of holes in glass substrates within microfluidics is well-known to the skilled person. A mask made from photoresist can be used to protect the electrodes and everything except for the inlet and outlet holes. This will provide a microfluidic particle analysis device 1 where the inlet manifold or the main channel is in fluid communication with the inlet 2 via a channel (not shown), which is orthogonal to the plane of the planar design. When the inlet 2 is in plane with the planar design of the measuring channel 11 and the bypass channel 12 the process step of creation of inlet and outlet holes on the top substrate is typically not employed.

In a third process step, the photoresist in which the channels are defined is patterned and deposited. For practical reasons the photoresist is typically applied to the bottom planar substrate using either spin- or spray-coating. Alternatively, the photoresist can also be laminated onto the substrate with a dry-film photoresist. In a specific fabrication process the photoresist is laminated onto the bottom substrate. The photoresist is patterned using a standard photolithography process with UV-exposure and development in an alkaline solution.

In a fourth process step the top and bottom substrates are aligned and bonded. The bonding process can be made prior to, or after, dicing. In a specific embodiment it is a direct bonding, in which the top and bottom substrates are aligned and subjected to temperature and pressure to seal the microfluidic channel. If the bonding process has been made prior to dicing, which is the most beneficial batch method, the final step is to dice the bonded wafers into separate chips.

The microfluidic particle analysis device 1 may now be finalised by connecting external components, e.g. tubes, pumps and electrical parts as appropriate.

In another embodiment, e.g. as illustrated in FIG. 7, the bypass channel 12 has a greater height, e.g. 200 µm, than the height of the measuring channel 11, e.g. 10 µm. The bypass channel 12 is defined in a glass, e.g. borosilicate, substrate using a standard hydrofluoric acid (HF)-etching process, while the measuring channel 11 is defined in a laminated dry-film photoresist. Silicon may also be used instead of borosilicate as a substrate in which case the bypass channel 12 can be defined using standard etching processes such as deep reactive ion etching. An advantage of using borosilicate is that one can optically determine if there is a fault in the chip from operation or from the fabrication.

In a first process step electrodes 14 are deposited onto a bottom substrate in order to produce a microfluidic particle analysis device 1 having coplanar electrodes 14, or the electrodes 14 are deposited onto a bottom and a top substrate in order to produce a microfluidic particle analysis device 1 having parallel overlapping electrodes 14. The electrodes 14 can be made using, in a cleanroom, a standard lift-off process with e-beam deposition of the electrode metals, e.g. Ti as adhesive layer and Au or Pt as conductive layer. The total thickness of the electrodes is usually between 100 and 200 nm.

In a second process step a standard HF-etch process is used to define the 100 µm deep channels 12 in both the bottom and top substrate. A backside protection layer is applied to the substrates and a standard photolithography process is used to define a mask with an etchant opening. Due to depth of the HF-etch it is advantageous to use a metal as a masking material, however, in order to protect the electrodes 14 during the metal mask stripping a thin intermediate photoresist layer between the metal mask and substrate can also be used. As an HF-etching process is an isotropic etch, the width of the channel 12 will be equal to the etching depth plus the mask opening. When the bypass channel 12 has been defined in the borosilicate substrate, the masking materials can be stripped accordingly.

A third process step may involve creation of the inlet and outlet holes on the top substrate (not shown), e.g. using powder blasting. Powder blasting of holes in glass substrates within microfluidics is well-known to the skilled person. A mask made from photoresist can be used to protect the electrodes 14 and everything except for the inlet and outlet holes. This will provide a microfluidic particle analysis device 1 where the inlet manifold or the main channel is in fluid communication with the inlet 2 via a channel (not shown), which is orthogonal to the plane of the planar design. When the inlet 2 is in plane with the planar design of the measuring channel and the bypass channel the process step of creation of inlet and outlet holes on the top substrate is typically not employed.

In a fourth process step a dry-film photoresist is laminated onto the bottom substrate. Due to an uneven typology from the HF-etching process, the photoresist cannot be spun onto the substrate, but spray-coating may be used, if the dry-film photoresist option is unavailable. The photoresist is patterned using a standard photolithography process with UV-exposure and development in an alkaline solution.

In a fifth process step the top and bottom substrates are aligned and bonded. The bonding process can be made prior to, or after, dicing. In a specific embodiment it is a direct bonding, in which the top and bottom substrates are aligned and subjected to temperature and pressure to seal the microfluidic channel. If the bonding process has been made prior to dicing, which is the most beneficial batch method, the final step is to dice the bonded wafers into separate chips.

The microfluidic particle analysis device 1 may now be finalised by connecting external components, e.g. tubes, pumps and electrical parts as appropriate.

The invention will now be explained in the following non-limiting examples. As will be evident to the skilled person variations are possible without deviating from the invention.

EXAMPLES

Example 1

To demonstrate proof of concept for the use of bypass channels in an impedance flow cytometer, four designs featuring bypass channels and measuring channels were made. The designs were made similar to system depicted in FIG. 1, but with three coplanar electrodes instead of two. The use of three coplanar electrodes allows for an accurate estimate of the transition time, and thus the flow rate, as the 2 µm polystyrene beads follow the laminar flow. The transition time and resulting flow rate was extracted as the peak-to-peak value in the differential measurement, see FIG. 6. The operational principle of differential measurements allows the impedance flow cytometer to be used as a flow sensor if the liquid has particles that follow the flow. The results are summarised in Table 1 and illustrated in FIG. 8.

Each design had two measuring channels, each with projected $X_{measuring}$ values of 2%, 5%, 10%, and 20%, respectively, for each microfluidic particle analysis device, and a single large bypass channel having flow distribution parameters of 96%, 90%, 80%, and 60%, respectively. Measurements were made on the four different bypass channel designs, with a total system flow rate set by an accurate syringe pump. The measurements were performed in a single measuring channel on a single set of electrodes. The flow in the measuring channel was found by using the volume in the channel from peak-to-peak signal as well as the transition time. According to theory the measuring channel flow rate would have to be proportional to the system flow rate, and it was expected that the flow rate in the measuring channel would directly correlate to the hydrodynamic resistance ratio between the measuring channel and the bypass channel. The results are summarised in Table 1.

The mismatch between the theoretical and experimental flow rate in the measuring channel is explained by the fabrication method. The lithography process used to transfer the channel pattern to a wafer demonstrated a tendency to make the channels slightly larger than anticipated. In this experimental setup, the channels were between 0.5 and 2 µm larger than in the mask design, which had a significant influence on the ratio between the measuring channels and the bypass channel. With dedicated manufacturing equipment the tolerances will be better, e.g. at ±0.5 µm. An optimised fabrication process would provide direct correlation between the measured and expected flow rate.

Figure 8:
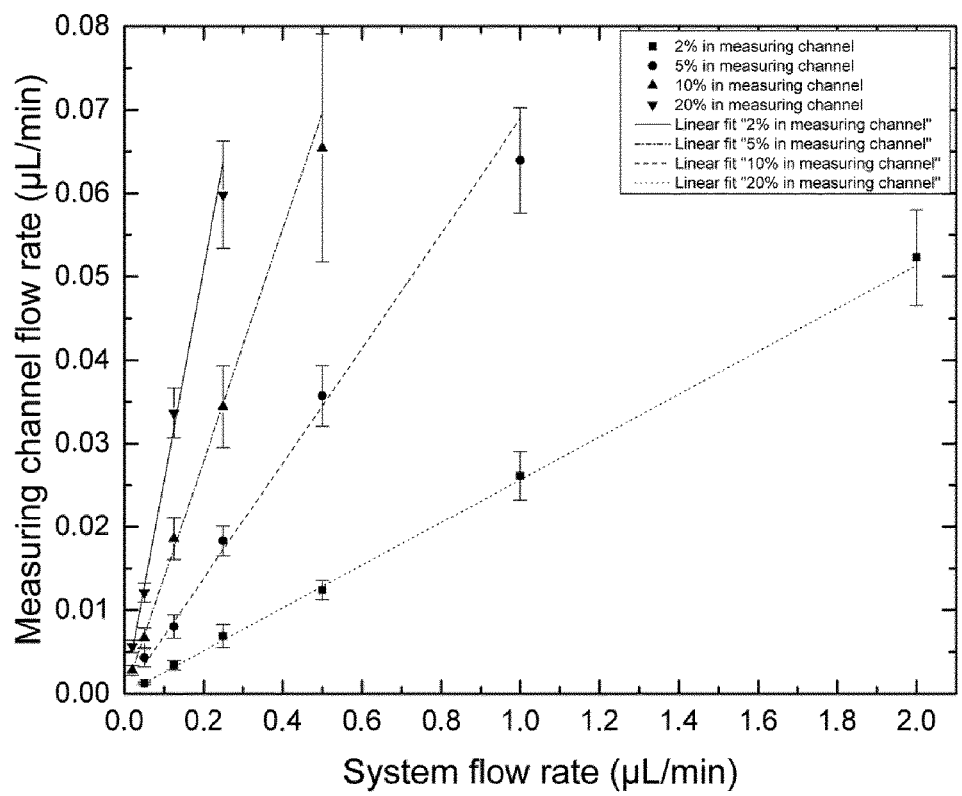
FIG. 8 illustrates particles distribution in embodiments of the invention.

A more detailed analysis can be made by examining the data. The flow rate in the measuring channel as a function of the flow rate induced by the syringe pump is used to demonstrate the working principle of the bypass channels, regardless of the fabrication uncertainties. As previously mentioned the flow rate of the measuring channel would have to be proportional to the flow rate in the entire system, in order to have successfully demonstrated the working principle of the bypass channel concept. The measuring channel flow rate as a function of the system flow in a chip with a "2% measuring channel", "5% in measuring channel", "10% in measuring channel", and "20% in measuring channel" design are shown in FIG. 8. It is evident that the flow in the measuring channel is proportional to the flow rate in the system, as one would expect.

Example 2

A microfluidic particle analysis device as illustrated in FIG. 5 was fabricated as described above to have a bypass channel with a height identical to the height of the measuring channel.

A microfluidic particle analysis system comprised a coarse filter (pore size 5 µm), a pressure-inducing unit, a flow-splitter, operating electronics, and the microfluidic particle analysis device. The flow splitter was introduced to increase the flow rate prior to the sample entering the microfluidic particle analysis device. The microfluidic particle analysis device was tested by introducing water to the inlet, and thereby to the measuring channel, and measuring a non-differential current. This value can be used to determine if there is water in the channel or not. Further functionality of the chip can be tested by introducing a known quantity of polystyrene beads (either 1 or 2 µm) and subsequently flushing the device to ensure it is clean and ready for operation, e.g. as outlined in Example 1 above.

Example 3

A microfluidic particle analysis device as illustrated in FIG. 5 was fabricated. The microfluidic particle analysis device had a bypass channel 12 of approximately 1800 µm length and a width of 500 µm. The length of the measuring channel 11 was about 1920 µm, and its width was 10 µm. The length of the main channel 15 was about 19,200 µm and its width was about 500 µm. All channels had a depth of 10 µm. The angle between the bypass channel 12 and the measuring channel 11, and thereby the angle of the measuring channel relative to the main flow direction, was about 30°. $X_{measuring}$ for this device was 0.008.

For comparison a device was manufactured where the angle between the bypass channel and the measuring channel was 90° (not shown). This device differed from the device of FIG. 5 and described above by having a measuring channel of about 1320 µm length and 10 µm width, a bypass channel with a length of about 1090 µm and a width of 500 µm, a main channel length of 19,800 µm and a width of 500 µm. $X_{measuring}$ for this device was 0.0063.

Both devices contained an EIS sensor set up as illustrated in FIG. 6.

The performance of the two devices was analysed by detecting particles after applying a flow of 2 µm polystyrene beads in water ($5.68 \cdot 10^6$ ml$^{-1}$) at a flow rate of 15 µl/min. The results are summarised in Table 2.

TABLE 2

Detection of particles in a microfluidic particle analysis device of the invention and in a comparison device

| Device | Recorded peaks | Time [s] | Flow rate [µl/min] | Concentration [beads/ml] |
|---|---|---|---|---|
| Invention | 616 | 58.95 | 15 | $5.22 \cdot 10^6$ |
| Comparison | 482 | 58.95 | 15 | $4.67 \cdot 10^6$ |

It is evident that the concentration measured in the microfluidic particle analysis device of the invention was about 12% higher than the concentration measured for the comparison device, and the concentration measured with the microfluidic particle analysis device of the invention was also much closer to the expected concentration. The measurement deviation between the two devices is believed to be caused by the inertial forces in the water. When the angle of the measuring channel relative to the main flow direction is larger than 60 degrees, i.e. 90 degrees in this example, the water pushes past the measuring channel inlet, and the amount of water in the measuring channel is less than what you would expect from a laminar flow system approximated to Stokes flow.

Figure 9:
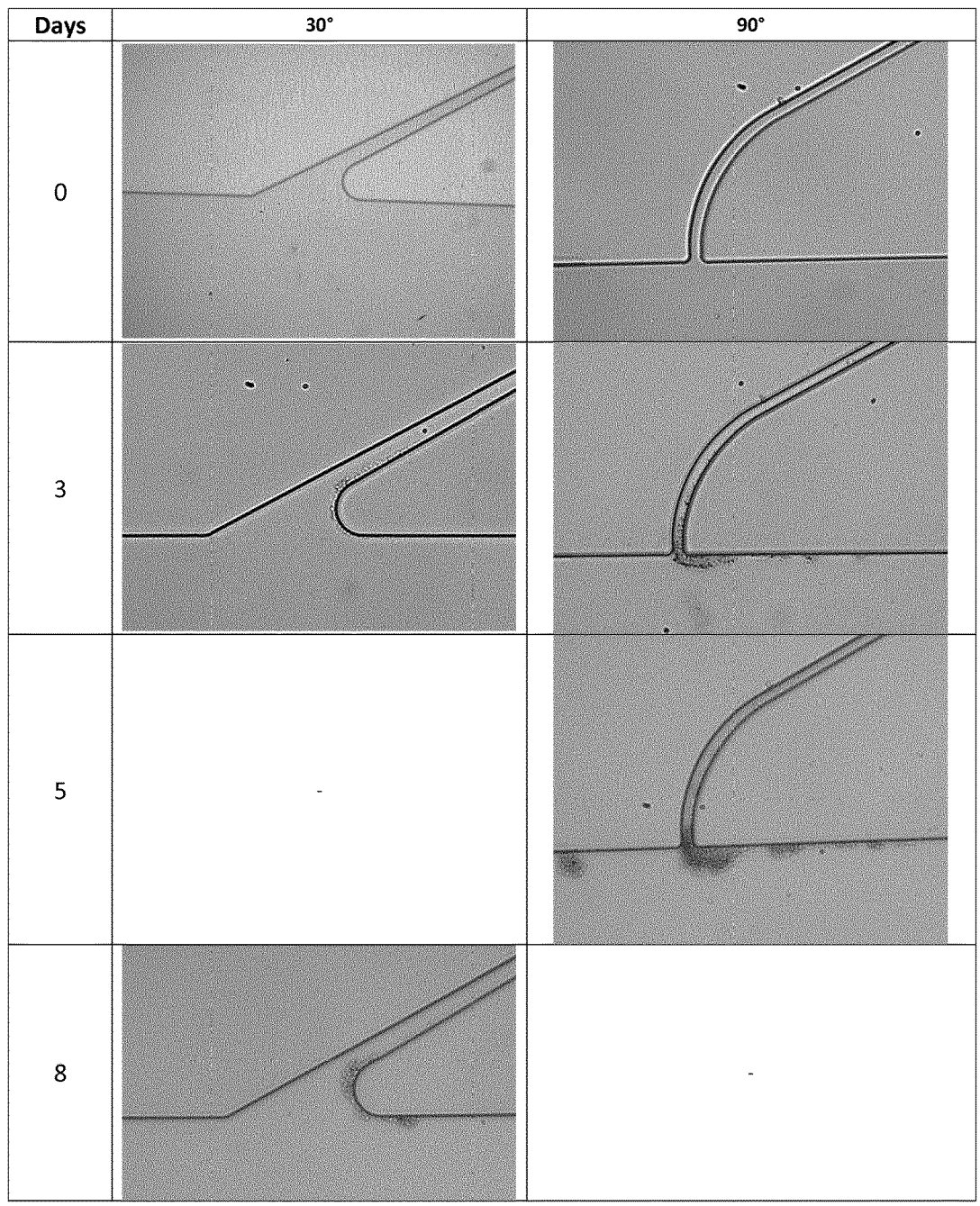
FIG. 9 compares experimental data for two designs of inlet manifolds.

The inertia of the water becomes particularly relevant in long term operation of the two devices. In order to compare long term operation of the two devices a flow of tap water (from Kongens Lyngby, Denmark), as a representative example of drinking water, was applied at a continuous volumetric flow rate of 30 µl/min over a period of 8 days. Before entering the devices the drinking water was filtered through a 10 µm pore-size filter. The inlet manifolds of the two devices were monitored using an optical microscope. Images were recorded at the start of the experiment and at daily intervals. FIG. 9 shows photomicrographs recorded at the start of the experiment and after 3 days for both devices. For the microfluidic particle analysis device of the invention (illustrated in FIG. 5) the photomicrograph taken after 8 days is shown, and for the comparison device the photomicrograph taken after 5 days is shown.

The results in FIG. 9 show that when the angle between the measuring channel and the bypass channel/the main channel was 90° the inlet of the measuring channel was clogged after only 3 days of operation. After 5 days the clog in the inlet had increased. Thus, the comparison device could not be used for long term monitoring of particles in a liquid, such as bacteria in drinking water. In contrast, the microfluidic particle analysis device did not experience any clogging of the inlet of the measuring channel.

Example 4

A microfluidic particle analysis device as illustrated in FIG. 7 was fabricated as described above to have a bypass channel of 200 µm×200 µm cross-sectional dimensions and two measuring channels of 10 µm×10 µm cross-sectional dimensions.

A microfluidic particle analysis system comprised a coarse filter (pore size 10 µm), a pressure-inducing unit, operating electronics, and the microfluidic particle analysis device. The flow-splitter can be omitted, as the value of $X_{measuring}$ was significantly larger than in the design where all channels are defined in a photoresist polymer, e.g. of Example 2. Similarly, the microfluidic particle analysis device was tested by introducing filtered water to the measuring channel and measuring a non-differential current. This value can be used to determine if there is water in the channel or not. Further functionality of the chip can be tested by introducing a known quantity of polystyrene beads (either 1 or 2 µm) and subsequently flushing the device to ensure it is clean and ready for operation, e.g. as outlined in Example 1 above.

Example 5

A microfluidic particle analysis device was fabricated as follows. A Pyrex glass wafer (0.5 mm thick) was hexamethyl-disilasane (HMDS) vapour-primed before a 1.5 µm layer of a reversible photoresist (AZ5214e, MicroChemicals) was spun on. After exposure and development, a 20 nm Cr adhesive layer and a 100 nm Au film were deposited by sputtering (QLC 800, Wordentec). The resulting electrode pattern, with 3 coplanar 10 µm wide electrodes and 5 µm pitch, was revealed by lift-off. The 10 µm wide measuring channel and 308 µm wide bypass channel were defined by spin coating a 5 µm layer of photosensitive SU8 (SU-8 2005, HD MicroChem), pre-baking (35° C.), exposing, developing, and post-baking (50° C.). Access holes with a diameter of 500 µm were drilled in a separate Pyrex wafer (0.5 mm thick) by using Silicon Carbide drill bits. The cleanroom processed wafer and wafer with access holes were aligned and assembled, and the bonding completed by ramped thermal treatment up to 180° C. while the two wafers were firmly pressed together (520 Hot Embosser, EV Group). The chips were subsequently diced (DAD 321, DISCO). During experiments, the fabricated microfluidic particle analysis devices were mounted in an aluminium custom built holder containing fluid connections and shielded connectors for the electrical readout in order to reduce the influence of external electrical noise. O-rings and spring-loaded contacts assured fast fluidic and electrical connections.

The measurements were carried out by applying an AC signal with an amplitude of 3V ($V_{peak-peak}$) and a frequency of 231 kHz to the excitation electrode. As opposed to regular impedance flow cytometry measurements, only one frequency was applied since multi-frequency characterisation of the sample was not necessary in order to determine the particle flow properties of the chips. Changes in the AC current between the electrodes were amplified by an HF2TA current amplifier (Zurich Instruments) and converted into a voltage signal and detected by an HF2IS Impedance Spectroscope (Zurich Instruments). The differential output current between the two outer electrodes was continuously recorded at a predetermined sample rate (e.g. 28800 samples/s) by a computer.

The invention claimed is:

1. A microfluidic particle flow analysis device comprising:
    an inlet in fluid communication via a main channel defining a main flow direction with an inlet manifold providing parallel fluid communication with
        a bypass channel of hydrodynamic resistance $R_{bypass}$, and
        a measuring channel of hydrodynamic resistance $R_{measuring}$, the measuring channel having a cross-sectional dimension in the range of 1 µm to 50 µm and further having a sensor system for detecting a particle,
    wherein a flow distribution parameter $X_{measuring}=R_{measuring}^{-1}(R_{measuring}^{-1}+R_{bypass}^{-1})^{-1}$ is in the range of $10^{-6}$ to 0.25, wherein the angle of the measuring channel relative to the main flow direction is in the range of 0° to 60°, and wherein the angle of the bypass channel relative to the main flow direction is in the range of 0° to 60°, and
    the microfluidic particle flow analysis device further comprises an outlet in fluid communication with the bypass channel and the measuring channel.

2. The microfluidic particle flow analysis device according to claim 1, wherein the sensor system for detecting a particle comprises a first electrode and a second electrode defining an operating space between the first electrode and the second electrode, which first and second electrodes are in electrical connection via an electric circuit comprising an alternating current (AC) or a direct current (DC) source and a device for monitoring an electrical signal from the first electrode and/or the second electrode.

3. The microfluidic particle flow analysis device according to claim 2, wherein the sensor system for detecting a particle on the same wall of the measuring channel comprises an excitation electrode located between two reference electrodes, or wherein the sensor system for detecting a particle comprises two sets of an excitation electrode and a reference electrode, where the excitation electrode and the reference electrode are positioned on opposite walls in the measuring channel.

4. The microfluidic particle flow analysis device according to claim 2, which does not employ hydrodynamic focusing or which does not employ dielectrophoretic focusing.

5. The microfluidic particle flow analysis device according to claim 1, wherein the bypass channel has a first cross-sectional dimension in the range of 50 µm to 300 µm and a second cross-sectional dimension in the range of 50 µm to 300 µm.

6. The microfluidic particle flow analysis device according to claim 1, wherein the measuring channel has a first cross-sectional dimension in the range of 5 µm to 20 µm and a second cross-sectional dimension in the range of 5 µm to 20 µm.

7. The microfluidic particle flow analysis device according to claim 1, wherein the bypass channel has a first cross-sectional dimension in the range of 50 µm to 300 µm and a second cross-sectional dimension in the range of 50 µm to 300 µm, the measuring channel has a first cross-sectional dimension in the range of 5 µm to 20 µm and a second cross-sectional dimension in the range of 5 µm to 20 µm and wherein the ratio of the length of the bypass channel to the length of the measuring channel is in the range of 10 to 200.

8. The microfluidic particle flow analysis device according to claim 7, wherein the ratio of the hydrodynamic resistance per length of channel of the measuring channel to the hydrodynamic resistance per length of the bypass channel is at least 500.

9. The microfluidic particle flow analysis device according to claim 1, wherein the measuring channel and the bypass channel have a cross-sectional dimension in the range of 5 µm to 100 µm.

10. The microfluidic particle flow analysis device according to claim 9, wherein the bypass channel has a second cross-sectional dimension in the range of 200 µm to 1000 µm.

11. The microfluidic particle flow analysis device according to claim 10, wherein the ratio of the hydrodynamic resistance per length of the measuring channel to the hydrodynamic resistance per length of the bypass channel is in the range of 50 to 500.

12. The microfluidic particle flow analysis device according to claim 1, wherein the angle between the measuring channel and the bypass channel is in the range of 0° to 60°.

13. The microfluidic particle flow analysis device according to claim 1, wherein the measuring channel defines an entry plane in the cross-section of the main channel, which entry plane is orthogonal to the main flow direction.

14. The microfluidic particle flow analysis device according to claim 1, wherein the microfluidic particle flow analysis device comprises a flow distribution device for receiving a flow of liquid from the inlet, which inlet is at an angle to a plane housing the flow distribution device, and which flow distribution device comprises from 2 to 8 collection channels positioned around an inlet point with each collection channel being in fluid communication with the main channel.

15. The microfluidic particle flow analysis device according to claim 1, wherein the length of the measuring channel is in the range of 10 µm to 5000 µm.

16. The microfluidic particle flow analysis device according to claim 1, wherein the features in the microfluidic particle flow analysis device have tolerances about ±1 µm.

17. A method of detecting a particle in a fluid, the method comprising:
providing a microfluidic particle flow analysis device comprising an inlet in fluid communication via a main channel defining a main flow direction with an inlet manifold providing parallel fluid communication with
a bypass channel of hydrodynamic resistance $R_{bypass}$, and
a measuring channel of hydrodynamic resistance $R_{measuring}$, the measuring channel having a cross-sectional dimension in the range of 1 µm to 50 µm and further having a sensor system for detecting a particle,
wherein a flow distribution parameter $X_{measuring} = R_{measuring}^{-1} (R_{measuring}^{-1} + R_{bypass}^{-1})^{-1}$ is in the range of $10^{-6}$ to 0.25, wherein the angle of the measuring channel relative to the main flow direction is in the range of 0° to 60°, and wherein the angle of the bypass channel relative to the main flow direction is in the range of 0° to 60°, and
the microfluidic particle flow analysis device further comprises an outlet in fluid communication with the bypass channel and the measuring channel;
providing a sample fluid;
applying a flow of the sample fluid from the inlet to the outlet of the microfluidic particle flow analysis device; and
detecting a particle having a dimension in the range of 0.1 µm to 10 µm, when present in the sample fluid, in the measuring channel using the sensor system for detecting a particle.

18. A method of monitoring a concentration of particles in a fluid, the method comprising:
providing a microfluidic particle flow analysis device comprising an inlet in fluid communication via a main channel defining a main flow direction with an inlet manifold providing parallel fluid communication with
a bypass channel of hydrodynamic resistance $R_{bypass}$, and
a measuring channel of hydrodynamic resistance $R_{measuring}$, the measuring channel having a cross-sectional dimension in the range of 1 µm to 50 µm and further having a sensor system for detecting a particle,
wherein a flow distribution parameter $X_{measuring} = R_{measuring}^{-1} (R_{measuring}^{-1} + R_{bypass}^{-1})^{-1}$ is in the range of $10^{-6}$ to 0.25, wherein the angle of the measuring channel relative to the main flow direction is in the range of 0° to 60°, and wherein the angle of the bypass channel relative to the main flow direction is in the range of 0° to 60°, and
the microfluidic particle flow analysis device further comprises an outlet in fluid communication with the bypass channel and the measuring channel;
providing a sample fluid containing particles having a dimension in the range of 0.1 µm to 10 µm;

applying a flow of the sample fluid from the inlet to the outlet of the microfluidic particle flow analysis device; and monitoring the concentration of the particles in the measuring channel using the sensor system for detecting a particle.

19. A method of detecting a particle in a fluid, the method comprising:
providing a microfluidic particle flow analysis device comprising an inlet in fluid communication via a main channel defining a main flow direction with an inlet manifold providing parallel fluid communication with a bypass channel of hydrodynamic resistance $R_{bypass}$, and
a measuring channel of hydrodynamic resistance $R_{measuring}$, the measuring channel having a cross-sectional dimension in the range of 1 μm to 50 μm and further having a sensor system for detecting a particle, which sensor system for detecting a particle comprises a first electrode and a second electrode defining an operating space between the first electrode and the second electrode, which first and second electrodes are in electrical connection via an electric circuit comprising an alternating current (AC) or a direct current (DC) source and a device for monitoring an electrical signal from the first electrode and/or the second electrode,
wherein a flow distribution parameter $X_{measuring}=R_{measuring}^{-1}(R_{measuring}^{-1}+R_{bypass}^{-1})^{-1}$ is in the range of $10^{-6}$ to 0.25, wherein the angle of the measuring channel relative to the main flow direction is in the range of 0° to 60°, and wherein the angle of the bypass channel relative to the main flow direction is in the range of 0° to 60°, and
the microfluidic particle flow analysis device further comprises an outlet in fluid communication with the bypass channel and the measuring channel;
providing a sample fluid;
applying a flow of the sample fluid from the inlet to the outlet of the microfluidic particle flow analysis device;
applying an AC or DC current from the current source to create an electric field in the operating space, and monitoring a differential electrical signal between the first electrode and the second electrode; and
detecting a particle having a dimension in the range of 0.1 μm to 10 μm, when present in the sample fluid, in the measuring channel using the differential electrical signal.

20. The method of detecting a particle in a fluid according to claim 17, wherein the concentration of particles in the sample fluid is in the range of 0 ml$^{-1}$ to $10^8$ ml$^{-1}$.

21. The method of detecting a particle in a fluid according claim 17, wherein a volumetric flow in the range of 10 μl/min to 10 ml/min is applied to the inlet of the microfluidic particle flow analysis device.

22. A method of monitoring the concentration of particles in a fluid, the method comprising:
providing a microfluidic particle flow analysis device comprising an inlet in fluid communication via a main channel defining a main flow direction with an inlet manifold providing parallel fluid communication with a bypass channel of hydrodynamic resistance $R_{bypass}$, and
a measuring channel of hydrodynamic resistance $R_{measuring}$, the measuring channel having a cross-sectional dimension in the range of 1 μm to 50 μm and further having a sensor system for detecting a particle, which sensor system for detecting a particle comprises a first electrode and a second electrode defining an operating space between the first electrode and the second electrode, which first and second electrodes are in electrical connection via an electric circuit comprising an alternating current (AC) or a direct current (DC) source and a device for monitoring an electrical signal from the first electrode and/or the second electrode,
wherein a flow distribution parameter $X_{measuring}=R_{measuring}^{-1}(R_{measuring}^{-1}+R_{bypass}^{-1})^{-1}$ is in the range of $10^{-6}$ to 0.25, wherein the angle of the measuring channel relative to the main flow direction is in the range of 0° to 60°, and wherein the angle of the bypass channel relative to the main flow direction is in the range of 0° to 60°, and
the microfluidic particle flow analysis device further comprises an outlet in fluid communication with the bypass channel and the measuring channel;
providing a sample fluid containing particles having a dimension in the range of 0.1 μm to 10 μm;
applying a flow of the sample fluid from the inlet to the outlet of the microfluidic particle flow analysis device;
applying an AC or DC current from the current source to create an electric field in the operating space; and
monitoring a concentration of the particles in the measuring channel by monitoring a differential electrical signal between the first electrode and the second electrode.

* * * * *